(12) United States Patent
Marzouk et al.

(10) Patent No.: US 11,585,794 B1
(45) Date of Patent: Feb. 21, 2023

(54) METHOD AND SYSTEM FOR GAS IDENTIFICATION BY SIMULTANEOUS PERMEATION THROUGH PARALLEL MEMBRANES

(71) Applicant: UNITED ARAB EMIRATES UNIVERSITY, Al Ain (AE)

(72) Inventors: Sayed A. M. Marzouk, Al Ain (AE); Abdullah J. Abu Namous, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/707,182

(22) Filed: Mar. 29, 2022

(51) Int. Cl.
*G01N 33/00* (2006.01)
*G01N 7/10* (2006.01)

(52) U.S. Cl.
CPC ......... *G01N 33/0022* (2013.01); *G01N 7/10* (2013.01); *G01N 33/0016* (2013.01); *G01N 33/0031* (2013.01); *G01N 33/0062* (2013.01); *G01N 33/0009* (2013.01); *G01N 2291/0215* (2013.01)

(58) Field of Classification Search
CPC .......... G01N 33/0022; G01N 33/0031; G01N 33/0062; G01N 33/0073; G01N 33/0009; G01N 2291/0215
USPC ...................................................... 73/31.05
See application file for complete search history.

(56) References Cited

U.S. PATENT DOCUMENTS 3,926,561 A * 12/1975 Lucero .................. B01D 53/22
436/139
4,858,461 A * 8/1989 Steinle ................. G01N 1/2273
73/31.04

FOREIGN PATENT DOCUMENTS

| CN | 100398182 C | * | 7/2008 | |
| EP | 2827144 A1 | * | 1/2015 | ......... G01N 33/0009 |
| WO | WO-2021182059 A1 | * | 9/2021 | |

* cited by examiner

*Primary Examiner* — Nathaniel J Kolb
(74) *Attorney, Agent, or Firm* — Hayes Soloway PC

(57) ABSTRACT

The present disclosure relates to a system and a method for gas fingerprinting. The system includes multiple holders having a distinct gas-permeable membrane disposed of therewithin such that a confined space is created behind the membranes. The test gas is pressurized in a single gas reservoir and is allowed to permeate through the membranes into respective confined spaces. The accumulated pressure values behind the utilized membranes (in the confined spaces) at a given time, are simultaneously recorded using pressure sensors. The recorded gas accumulation data is processed by a computing device to determine a characteristic property for each test gas. The system ability to fingerprint gases is demonstrated by ten test gases including helium, neon, argon, hydrogen, nitrogen, carbon dioxide, methane, ethane, propane, and ethylene, and is also able to discriminate between closely related gases.

20 Claims, 17 Drawing Sheets

300

```
┌─────────────────────────────────────────────────────────────────────────────┐
│ ALLOWING A SIMULTANEOUS PARALLEL FLOW OF THE TEST GAS THROUGH A PLURALITY   │
│ OF PARALLELLY CONFIGURED HOLDERS, WHEREIN EACH OF THE HOLDERS COMPRISES A   │
│ DISTINCT GAS PERMEABLE MEMBRANE DISPOSED OF THEREWITHIN SUCH THAT THE       │
│ MEMBRANES ARE CONFIGURED PARALLELLY AND A CONFINED SPACE IS CREATED BEHIND  │
│ EACH OF THE MEMBRANES                                                       │
│ 302                                                                         │
└─────────────────────────────────────────────────────────────────────────────┘
                                      │
                                      ▼
┌─────────────────────────────────────────────────────────────────────────────┐
│ ALLOWING PERMEATION OF AT LEAST A VOLUME OF THE SUPPLIED TEST GAS THROUGH   │
│ THE RESPECTIVE MEMBRANES FOR A PREDEFINED TIME, RESULTING IN ACCUMULATION   │
│ OF THE PERMEATED TEST GAS IN THE CONFINED SPACE BEHIND THE RESPECTIVE       │
│ MEMBRANES                                                                   │
│ 304                                                                         │
└─────────────────────────────────────────────────────────────────────────────┘
                                      │
                                      ▼
┌─────────────────────────────────────────────────────────────────────────────┐
│ MONITORING, BY A PRESSURE SENSOR CONFIGURED IN THE CONFINED SPACES BEHIND   │
│ EACH OF THE MEMBRANES, RATE OF TEST GAS PRESSURE ACCUMULATION IN THE        │
│ CORRESPONDING CONFINED SPACES                                               │
│ 306                                                                         │
└─────────────────────────────────────────────────────────────────────────────┘
                                      │
                                      ▼
┌─────────────────────────────────────────────────────────────────────────────┐
│ RECEIVING, BY A COMPUTING UNIT, A FIRST SET OF DATA PACKETS CORRESPONDING   │
│ TO THE RATE OF TEST GAS PRESSURE ACCUMULATION IN THE CONFINED SPACES BEING  │
│ MONITORED BY THE PRESSURE SENSORS                                           │
│ 308                                                                         │
└─────────────────────────────────────────────────────────────────────────────┘
                                      │
                                      ▼
┌─────────────────────────────────────────────────────────────────────────────┐
│ PERFORMING, BY THE COMPUTING UNIT, SEMI-QUANTITATIVE ANALYSIS OF THE TEST   │
│ GAS, BASED ON THE FIRST SET OF DATA PACKETS, TO IDENTIFY THE TEST GAS OR A  │
│ PERCENTAGE OF GAS IN GAS MIXTURE                                            │
│ 310                                                                         │
└─────────────────────────────────────────────────────────────────────────────┘
```

*FIG. 3*

METHOD AND SYSTEM FOR GAS IDENTIFICATION BY SIMULTANEOUS PERMEATION THROUGH PARALLEL MEMBRANES

FIELD OF THE INVENTION

The present disclosure relates to the field of gas identification systems and methods. More particularly, the present disclosure relates to a novel and, efficient approach for gas identification/fingerprinting for the construction of portable and reliable electronic noses, which allows simultaneous identification of gases and gas mixtures and is also able to discriminate between closely related gases.

BACKGROUND OF THE INVENTION

Background description includes information that will be useful in understanding the present invention. It is not an admission that any of the information provided herein is prior art or relevant to the presently claimed invention, or that any publication specifically or implicitly referenced is prior art.

Gas identification is widely required in several fields such as medical, industrial, alarming, military, and security applications. Several analytical instrumental techniques are available in the prior art for the identification of gases. These techniques include infra-red spectroscopy, mass spectrometry, Raman spectroscopy, photoacoustic spectroscopy, and electronic noses systems that are based on different types of sensor arrays. Nowadays, electronic nose systems are the primary gas identification means, which typically involve an array of sensors, signal acquisition and processing, pattern recognition, and reference database. Generally, distinct chemical sensors specific to a single gas type are not required in the electronic nose systems. Instead, sensors array in electronic nose upon detecting the specific gas generate and transmit a set of signals to a processing unit that recognizes a pattern in the signals and compares them with a large database of known reference signals, to identify the corresponding gas. Accordingly, multiple numbers of such sensors are required to identify the composition of a gas mixture of different gases.

The common sensor types utilized in existing electronic noses are metal oxide semiconductors, chemiresistive, electrochemical sensors, gravimetric (SAW, BAW, QCM, etc.), and colorimetric and fluorometric. However, the sensors used in the construction of existing electronic noses suffer from one or more limitations such as moisture sensitivity, need for high temperature, not being capable of detecting multiple gases or gas mixture composition, or not being matured for commercialization. Besides, these sensors are typically responsive to limited group or groups of gases.

There is, therefore, a need to overcome the above-mentioned drawbacks, limitations, and shortcomings associated with exiting gas identification techniques and provide an improved, and efficient approach for gas identification/fingerprinting for the construction of portable and reliable electronic noses, applicable for the identification of, in principle, of any gas or gas mixture and is also able to discriminate between closely related gases.

SUMMARY OF THE INVENTION

The present disclosure relates to a novel, and efficient approach for gas identification/fingerprinting for the construction of portable and reliable electronic noses, which allows identification of, in principle, any gas and is also able to discriminate between closely related gases.

An aspect of the present disclosure pertains to a system and method for gas fingerprinting based on simultaneous gas permeation through different membranes. The test gas, which may either be a pure gas or a gas mixture, may be pressurized in a single compartment (gas reservoir) and may be allowed to permeate through multiple gas permeable membranes into respective confined spaces behind the membranes. The accumulated pressure values behind the utilized membranes (in the confined spaces) at a given time (t), may be simultaneously recorded to determine a characteristic property for each gas. The selected membranes may not be selective for any gas but rather may exhibit different permeabilities for different gases, such that the overall selectivity is based on the permeation pattern exhibited by different membranes.

The present invention (system and method) may involve a multi-channel system comprising multiple holders connected to a pressurized gas reservoir storing the test gas. Each holder may comprise a distinct gas permeable membrane removably disposed of therewithin such that the membranes are configured parallelly, and a confined space is created behind each of the membranes. Further, pressure sensors may be installed in confined spaces. The holder may be arranged over a gas discharge unit that may act as a base and may also enable the simultaneous flow of the stored test gas through the membranes of each of the holders, which when results in permeation the supplied test gas through the respective membranes, may cause accumulation of the permeated test gas in the confined space behind the respective membranes. The pressure sensors may monitor the rate of test gas pressure accumulation in the corresponding confined spaces, which may be indicative of a rate of permeation of the test gas through the corresponding membrane. Furthermore, the data captured by the pressure sensors may be processed by a computing unit to identify the test gas or its composition and determine the characteristics of the test gas.

The simultaneous permeation rates through different membranes may provide a very promising potential as characteristic fingerprints for the ten test gases, i.e., helium, neon, argon, hydrogen, nitrogen, carbon dioxide, methane, ethane, propane, and ethylene, which may be selected as representative examples of mono-, di-, tri- and polyatomic gases and to include some homologous series and to be able to test the potential of the proposed system to discriminate between closely related gases such as ethane and ethylene or carbon dioxide and propane which have almost identical molecular masses. The utilized gas permeable membranes may comprise Teflon AF®, Silicone Rubber, track-etch hydrophilic polycarbonate, track-etch hydrophobic polycarbonate, track-etch polyimide, nanoporous anodic aluminum oxide, Zeolite ZSM-5, and Zeolite Nay.

Thus, the present invention provides an improved, and efficient approach for gas identification/fingerprinting for the construction of portable and reliable electronic noses, which allows simultaneous identification of gases or gas mixtures and is also able to discriminate between closely related gases. Besides, the non-requirement of temperature and moisture-sensitive chemical-based gas sensors in the present invention, makes it reliable, robust, and less prone to failure. In addition, the number of membranes can be limited up to 4 or 5, which may further help in system miniaturization as required. The present invention may be simplified by employing micro and wireless sensors, along with a single cover that may hold the needed 4-5 sensors in the confined spaces behind the membranes. This may enable the construction of portable and reliable electronic noses.

Further, membrane holders and cover for the sensors may be made using thick transparent acrylic sheets for a required thickness, and sealant (O-ring) may also be employed, which may restrict gas leakage. Furthermore, the volume of the pressurized gas reservoir may be kept significantly larger than the combined volume of the holders and gas discharge unit. This may enable accurate monitoring of the rate of test gas pressure accumulation in the corresponding confined spaces behind the membranes.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings. In the figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 3 illustrates an exemplary flow diagram of the proposed gas identification method, in accordance with an embodiment of the present invention.

DETAILED DESCRIPTION OF THE INVENTION

Figure 1:
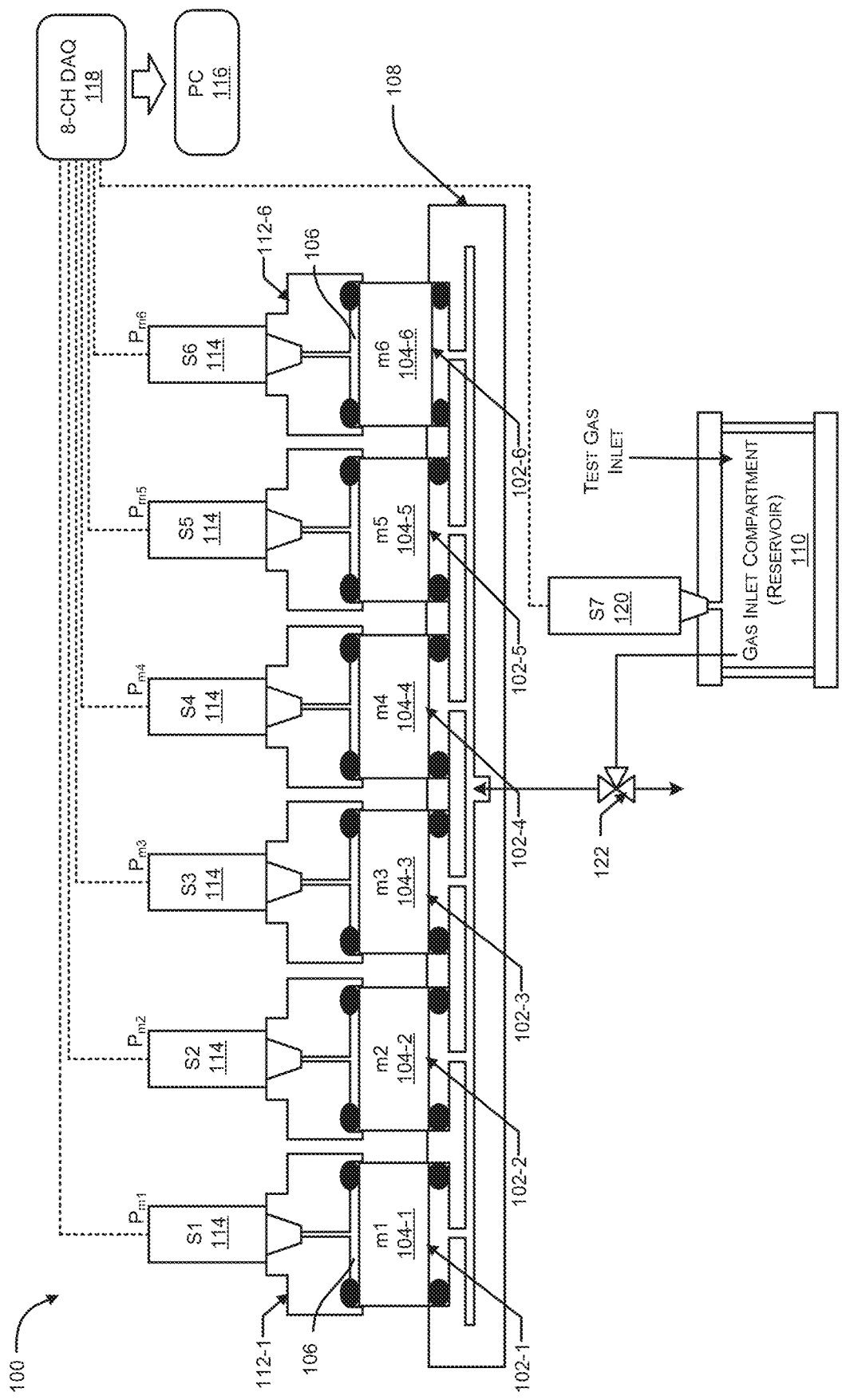
FIG. 1 illustrates an exemplary setup of the proposed gas identification system, in accordance with an embodiment of the present invention.

The aspects of an efficient approach for gas identification/fingerprinting for the construction of portable and reliable electronic noses, according to the present invention will be described in conjunction with FIGS. 1-10D. In the Detailed Description, reference is made to the accompanying figures, which form a part hereof, and in which is shown by way of illustration specific embodiments in which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

If the specification states a component or feature "may", "can", "could", or "might" be included or have a characteristic, that particular component or feature is not required to be included or have the characteristic. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced items. Further, the use of terms "first", "second", and "third", and the like, herein do not denote any order, quantity, or importance, but rather are used to distinguish one element from another. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It is an object of the present disclosure to overcome the above-mentioned drawbacks, limitations, and shortcomings associated with exiting gas identification techniques. It is an object of the present disclosure to enable simultaneous identification of any gas or gas mixture. It is an object of the present disclosure to simultaneously identify test gas or a gas mixture comprising, but not limited to, any or a combination of helium, argon, hydrogen, nitrogen, carbon dioxide, methane, ethane, propane, and ethylene. It is an object of the present disclosure to provide a gas identification approach that is also able to discriminate between closely related gases such as ethane and ethylene or carbon dioxide and propane, and the likes, which have almost identical molecular masses.

It is an object of the present disclosure to provide a gas identification approach that does not require moisture and temperature-sensitive gas sensors. It is an object of the present disclosure to provide a gas identification approach that identifies any gas or gas mixture based on simultaneous permeation rate of a pressurized test gas through distinct gas permeable membranes, which requires only a simple pressure sensor which by itself does not impart any chemical recognition of the test gas/gas mixture. It is an object of the present disclosure to provide an improved, and efficient approach for gas identification/fingerprinting for the construction of portable and reliable electronic noses. It is an object of the present disclosure to provide an improved, and efficient system and method for simultaneous identification of any gas or gas mixture based on simultaneous permeation rate of a pressurized test gas through distinct gas permeable membranes, which is also able to discriminate between closely related gases.

The present disclosure relates to an improved, and efficient approach for gas identification/fingerprinting for the construction of portable and reliable electronic noses, which allows identification of any gas/gas mixture and is also able to discriminate between closely related gases.

According to an aspect, the present disclosure elaborates upon a system for identification of test gas. The system can include a plurality of parallelly configured holders, each including a distinct gas permeable membrane removably disposed therewithin such that the membranes are configured parallelly, and a confined space is created behind each of the membranes. The system can be configured to enable a simultaneous flow of a test gas through the membranes of each of the holders, which when results in permeation of at least a volume of the supplied test gas through the respective membranes, can cause accumulation of the permeated test gas in the confined space behind the respective membranes. The system can include a pressure sensor configured in the confined space behind each of the membranes. The pressure sensor can be configured to monitor the rate of test gas pressure accumulation in the corresponding confined spaces, and can correspondingly generate a first set of signals indicative of a rate of permeation of the test gas through the corresponding membrane, which can facilitate in the determination of one or more characteristics of the test gas.

In an embodiment, the system can include a gas reservoir configured to store the test gas at a predefined pressure. The gas reservoir can be fluidically coupled to the plurality of holders and configured to enable the simultaneous flow of the stored test gas through the membranes of each of the holders. In an embodiment, the plurality of holders can be vertically arranged on and fluidically coupled to a gas distribution unit, such that the gas distribution unit can allow the simultaneous parallel flow of the test gas, from the gas reservoir, into the membranes. In an embodiment, the plurality of holders can be fluidically coupled to the gas reservoir and the gas distribution unit through a set of conduits and a two-way valve. In an embodiment, the volume of the gas reservoir can be kept greater than the total internal volume of the plurality of holders and the gas distribution unit combined. In an embodiment, the system can include a cover disc made of a thick transparent acrylic sheet being configured with the plurality of holders to create the confined spaces behind each of the membranes.

In an embodiment, the cover disc can be configured to accommodate the pressure sensor thereon and allow accumulation of the permeated gas in the corresponding spaces behind the membranes. In an embodiment, the system can include an O-ring positioned in between each of the holders and the corresponding cover disc to restrict leakage of the test gas therefrom. In an embodiment, the system can include a ball valve fluidically configured with each of the cover discs through a conduit. The ball valve can be configured to facilitate controlled outflow of the test gas or air from the system. In an embodiment, at least one of the plurality of holders can be a sandwich-type holder including a first disc having a first channel, and a second disc having a second channel. Further, at least one of the first disc, and the second disc can include a groove at one end, such that when adjacent surfaces of the first disc and the second disc are connected to form the sandwich-type holder, a cavity is created between the first disc and the second disc, with the first channel and the second channel fluidically connected to the created cavity. In an embodiment, the holder can include a porous supporting disc configured within the cavity and oriented parallel to the adjacent connected surfaces of the first disc and second disc. The porous supporting disc can be configured to hold the membrane within the cavity of the sandwich-type holder.

In an embodiment, the first disc and the second disc can be coaxially coupled to each other through a set of fasteners such that the first channel and the second channel are in line and fluidically connected to the cavity. The confined space can be behind the second disc, which can be in fluidic communication with the second channel of the sandwich-type holder. In an embodiment, the sandwich-type holder can include a set of O-rings configured on each side of the porous supporting disc within the cavity to restrict leakage of the test gas. In an embodiment, at least one of the holders can have a disc-shaped profile adapted to accommodate the membrane selected from Zeolite ZSM-5, and Zeolite Nay. The disc-shaped holder can be made of thick transparent acrylic sheet and comprises at least one channel extending between a first end and a second end of the disc, such that the corresponding membrane is longitudinally disposed within the at least one channel, with a thin cured epoxy layer provided between the surfaces of the membrane and the channel. In an embodiment, the test gas can be selected from any or a combination of helium, argon, hydrogen, nitrogen, carbon dioxide, methane, ethane, propane, and ethylene. In an embodiment, the distinct membranes can be selected from Teflon AF®, Silicone Rubber, track-etch hydrophilic polycarbonate, track-etch hydrophobic polycarbonate, track-etch polyimide, nanoporous anodic aluminum oxide, Zeolite ZSM-5, and Zeolite Nay.

In an embodiment, each of the pressure sensors can be in communication with a computing device that can be configured to receive the first set of signals from the pressure sensors and correspondingly perform semi-quantitative analysis of the test gas to determine the one or more characteristics of the test gas. In an embodiment, the computing unit can be configured to control an input valve to enable inflow of the test gas within the gas reservoir, through an inlet of the gas reservoir, to maintain the predefined pressure within the gas reservoir. Further, the computing unit can control the two-way valve to enable the outflow of the test gas from an outlet of the gas reservoir into the plurality of holders. Further, the computing unit can control the ball valve to enable venting of the accumulated gas out of the holders and the system. In another embodiment, the input valve can be manually controlled by a user to enable inflow of the test gas within the gas reservoir, through the inlet of the gas reservoir, to maintain the predefined pressure within the gas reservoir. Further, the two-way valve can also be manually controlled by the user to enable the outflow of the test gas from the outlet of the gas reservoir into the plurality of holders. Furthermore, the user can also manually control the ball valve to enable venting of the accumulated gas out of the holders and the system. According to another aspect, the present disclosure elaborates upon a method for the identification of test gas. The method can include steps of allowing a simultaneous parallel flow of the test gas through a plurality of parallelly configured holders, wherein each of the holders comprises a distinct gas permeable membrane disposed of therewithin such that the membranes are configured parallelly and a confined space is created behind each of the membranes. Further, the method can include a step of allowing permeation of at least a volume of the supplied test gas through the respective membranes for a predefined time, resulting in accumulation of the permeated test gas in the confined space behind the respective membranes, followed by another step of monitoring, by a pressure sensor configured in the confined spaces behind each of the membranes, rate of test gas pressure accumulation in the corresponding confined spaces. The monitored rate of test gas pressure accumulation can be indicative of a rate of permeation of the test gas through the corresponding membrane, which can facilitate determining one or more characteristics of the test gas.

In an embodiment, the method can include a step of receiving, by a computing unit, a first set of data packets corresponding to the rate of test gas pressure accumulation in the confined spaces being monitored by the pressure sensors, and another step of performing, by a user the computing unit, semi-quantitative analysis of the test gas, based on the first set of data packets, to determine the one or more characteristics of the test gas. The user can manually perform the semi-quantitative analysis of the test gas. Further, the computing unit can also perform the semi-quantitative analysis of the test gas. Referring to FIG. 1, the proposed system 100 for gas identification or fingerprinting can include a plurality of parallelly configured membrane holders 102-1 to 102-6 (collectively referred to as holders 102, herein). Each holder 102 can include a distinct gas-permeable membrane (m1-m6) 104-1 to 104-6 (also referred to as membrane 104, herein) being removably disposed of therewithin such that the membranes 104 are configured parallelly and a confined space 106 is created behind each membrane 104. This also facilitates easier replacement of the membranes 104 from the holders 102 when required. The system 100 can include a gas reservoir 110 (also referred to as inlet gas compartment 110, herein) that can be adapted to store a test gas at a predefined pressure. The system 100 can further include a gas discharge unit 108 that can act as a base for the holders 102, such that the holders 102 are vertically arranged on top of the gas distribution unit 108, and the holders 102 are also fluidically coupled to the gas distribution unit 108. Further, the gas reservoir 110 can be fluidically coupled to the gas distribution unit 108 through a set of conduits and a two-way valve 122. Accordingly, the gas distribution unit 108 and the two-way valve 122 can enable the simultaneous parallel flow of the test gas, from the gas reservoir 102, into the membranes 104 installed within the holders 102.

In an embodiment, the gas reservoir 110 can include an inlet fitted with an input valve to enable inflow and storage of the test gas within the gas reservoir 110 and help maintain the predefined pressure within the gas reservoir 110. Further, the outlet of the reservoir 110 can be fluidically coupled to the inlet of the gas distribution unit 108 through the set of conduits and valve 122. The valve 122 can enable the flow of the stored test gas into the holders 102 through the gas distribution unit 108. Furthermore, the gas distribution unit 108 can include a plurality of outlets equal to the number of holders 102 configured over it. These outlets can be adapted to accommodate the holders 102 in a vertical position thereon. The outlets can be further internally connected to the single inlet of the gas distribution unit 108 through channels, such that all the holders 102-1 to 102-6 can simultaneously receive the test gas and allow the simultaneous parallel flow of the test gas through the membranes 104. In an embodiment, the test gas can be selected from any or a combination of helium, argon, hydrogen, nitrogen, carbon dioxide, methane, ethane, propane, and ethylene, but not limited to the likes. In another embodiment, the distinct membranes 104-1 to 104-6 can be selected from Teflon AF®, Silicone Rubber, track-etch hydrophilic polycarbonate, track-etch hydrophobic polycarbonate, track-etch polyimide, nanoporous anodic aluminum oxide, Zeolite ZSM-5, and Zeolite Nay, but not limited to the likes.

The simultaneous flow of the test gas through the membranes 104 of each holder 102, when results in permeation of at least a volume of the supplied test gas through the respective membranes, can cause accumulation of the permeated test gas in the confined space 106 behind the respective membranes 104. The rate of test gas pressure accumulation in the corresponding confined spaces 106 can be indicative of the rate of permeation of the test gas through the corresponding membrane 102, which constitute characteristic fingerprint for the test gas. The system can include a pressure sensor (S1-S6) 114 configured in the confined space 106 behind each membrane 104. The pressure sensors 114 can be configured to monitor the rate of test gas pressure accumulation in the corresponding confined spaces 106, and can correspondingly generate a first set of signals indicative of a rate of permeation of the test gas through the corresponding membrane, which can facilitate in determining the characteristics of the test gas. Further, the system 100 can include a computing unit 116 in communication with each of the pressure sensors 114. The computing unit 116 can be configured to receive the first set of signals from the pressure sensors 114 and can correspondingly perform semi-quantitative analysis of the test gas in a mixture or to identify the test gas. In an embodiment, the gas reservoir 110 can also include another pressure sensor (S7) 120 that can be in communication with the computing unit 116. This pressure sensor 120 can monitor the pressure of the test gas inside the gas reservoir 110 so that a user and/or the computing unit 116 can accordingly control the input valve of the gas reservoir 110 to maintain the predefined pressure of the test gas within the reservoir 110.

In an embodiment, the system 100 can include a ball valve 124 (see FIG. 2C) configured with each holder 102 and in communication with the computing unit 116, The ball valve 124 can enable venting of the accumulated test gas or air out of the holders 102 and the system 100, to make the system ready for the gas identification process. In an embodiment, a cover disc 112-1 to 112-6 (collectively referred to as cover disc 112, herein) can be configured with each holder 102 to create the confined spaces 106 behind each membrane 104. The cover disc 112 can also accommodate the pressure sensor 114 thereon and can allow the accumulation of the permeated gas in the corresponding spaces 106. A single cover can also be used to accommodate the holders and create the confined space in each membrane 104, which can help make the proposed system 100 simple and portable.

Figure 2A:
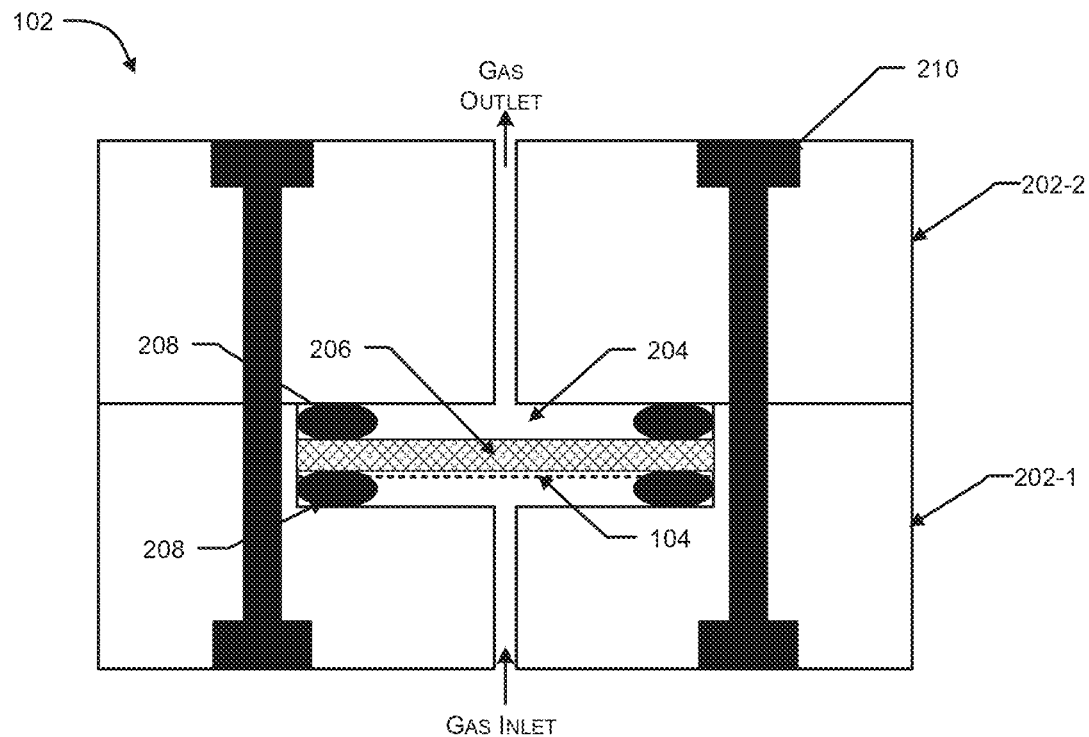
FIG. 2A illustrates an exemplary cross-section view of a sandwich-type holder used in the proposed system, in accordance with an embodiment of the present invention.
Figure 2B:
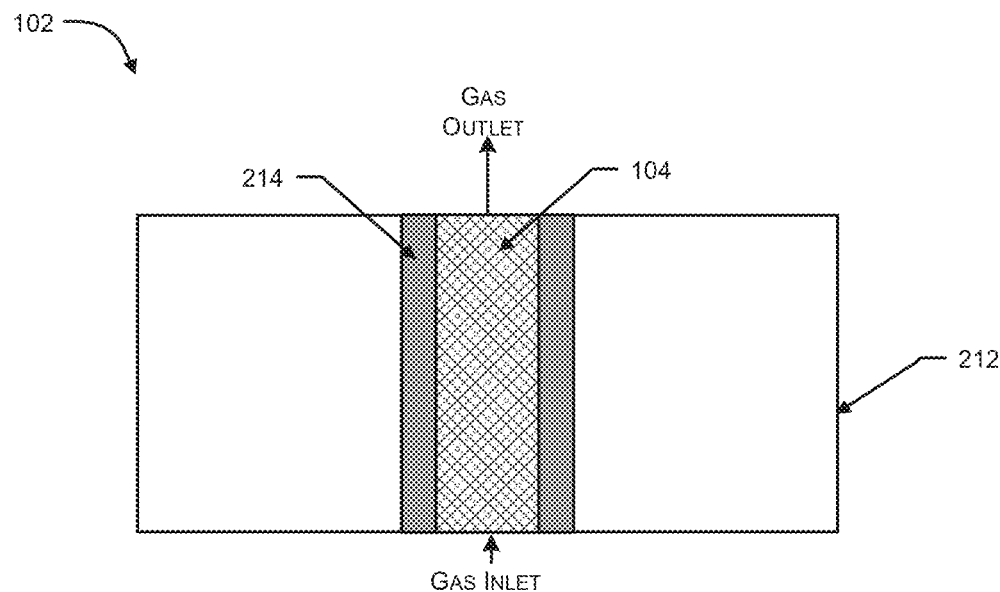
FIG. 2B illustrates an exemplary cross-section view of a disc-shaped holder used in the proposed system for Zeolite-based membranes, in accordance with an embodiment of the present invention.

Referring to FIG. 2A, in an embodiment, at least one of the holders 102 can be a sandwich-type holder used for thin membranes 104 like Polycarbonate, Polyimide, Teflon AF®, Silicon rubber, and Aluminum Oxide. The sandwich-type holder 102 can include a first disc 202-1 having a first channel, and a second disc 202-2 having a second channel. Further, at least one of the first disc 202-1, and the second disc 202-2 can include a groove at one end, such that when adjacent surfaces of the first disc 202-1 and the second disc 202-2 are connected to form the sandwich-type holder, a cavity 204 is created between the first disc 202-1 and the second disc 202-2, with the first channel and the second channel fluidically connected to the created cavity 204. Further, the holder 102 can include a porous supporting disc 206 configured within the cavity 204 and oriented parallel to the adjacent connected surfaces of the first disc 202-1 and second disc 202-2. The porous supporting disc 206 can be configured to hold the thin membrane 104 within the cavity 204 of the sandwich-type holder 102. As shown in FIG. 2A, the first disc 202-1, and the second disc 202-2 can be coaxially coupled to each other through a set of fasteners 210 (SS bolts, and the likes) such that the first channel and the second channel are in line and fluidically connected to the cavity 204. Further, the confined space 106 can be behind the second disc 202-2, which can be in fluidic communication with the second channel of the sandwich-type holder 102. Furthermore, the sandwich-type holder can include a set of O-rings 208 configured on each side of the porous supporting disc 206 within the cavity 204 to restrict leakage of the test gas while flowing therethrough. Referring to FIG. 2B, in another embodiment, at least one of the holders 102 can have a disc-shaped profile adapted to accommodate the membrane selected from Zeolite ZSM-5, and Zeolite Nay. The disc-shaped holder 102 can include at least one channel extending between a first end and a second end of the disc 212, such that the corresponding membrane 104 is longitudinally disposed within at least one channel, with a thin cured epoxy layer 214 provided between the surfaces of the membrane 104 and the disc 212.

In an exemplary embodiment, the disc-shaped holder and the sandwich-type holder can be made of thick transparent acrylic sheets, but not limited to the like.

Referring to FIG. 3, exemplary steps involved in the proposed method 300 for gas identification is disclosed, The proposed method 300 can include step 302 of allowing a simultaneous parallel flow of the test gas through the parallelly configured holders or channels, followed by another step 304 of allowing permeation of at least a volume of the test gas (supplied at step 302) through the respective membranes for a predefined time, resulting in accumulation of the permeated test gas in the confined space behind the respective membranes. Further, method 300 can include step 306 of monitoring, by a pressure sensor configured in the confined spaces behind each of the membranes, rate of test gas pressure accumulation in the corresponding confined spaces. This monitored rate of test gas pressure accumulation can be indicative of a rate of permeation of the test gas through the corresponding membrane, which facilitates determining one or more characteristics of the test gas. In an embodiment, method 300 can include a step 308 of receiving, by a computing unit, a first set of data packets corresponding to the rate of test gas pressure accumulation in the confined spaces being monitored by the pressure sensors, followed by another step 310 of performing, by the computing unit, semi-quantitative analysis of the test gas, based on the first set of data packets, to identify the test gas or a percentage of a gas in a gas mixture. Those skilled in the art would appreciate that the data pertaining to the rate of permeation of the test gas through at least one of the channels or membrane is sufficient for the semi-quantitative analysis to identify the percentage of gas in the gas mixture.

Considering an exemplary experimental setup in accordance with the present invention, details of all membranes are provided in Table 1 below.

TABLE 1

| | Membrane | Abbreviation | Source | Specifications |
|---|---|---|---|---|
| 1 | Polycarbonate | PC-1 | SPI | 25-mm dia., 6-µm thick, pore diameter 0.01 µm (Hydrophilic) |
| 2 | Polycarbonate | PC-2 | it4ip | 25-mm dia., 10-µm thick, pore density $3 \times 10^9$ cm$^{-2}$, pore diameter 0.01 µm (Hydrophilic) |
| 3 | Polycarbonate | PC-3 | | 25-mm dia., 25-µm thick, pore density $4 \times 10^9$ cm$^{-2}$, pore diameter 0.01 µm (Hydrophilic) |
| 4 | Polycarbonate | PC-4 | | 25-mm dia., 50-µm thick, pore density $2 \times 10^9$ cm$^{-2}$, pore diameter 0.01 µm (Hydrophilic) |
| 5 | Polycarbonate | PC-5 | | 25-mm dia., 50-µm thick, pore density $2 \times 10^9$ cm$^{-2}$, pore diameter 0.01 µm (Hydrophobic) |
| 6 | Polyimide | PI-1 | | 25-mm dia., 25-µm thick, pore density $1 \times 10^9$ cm$^{-2}$, pore diameter 0.01 µm (Hydrophilic) |
| 7 | Polyimide | PI-2 | | 13-mm dia., 25-µm thick, pore density $6 \times 10^9$ cm$^{-2}$, pore diameter 0.01 µm (Hydrophilic) |
| 8 | PEEK-20 | PEEK-20 | Sterlitech | 25-mm dia., pore diameter 0.02 µm |
| 9 | PVDF-20 | PVDF-20 | | 25-mm dia., pore diameter 0.02 µm |
| 10 | Teflon AF ® | T-AF1 | Biogeneral Inc. | 47-mm dia., 40-µm thick. |
| 11 | Silicon | SR | AAA- | 47-mm dia., 128-µm thick. |

TABLE 1-continued

| Membrane | Abbreviation | Source | Specifications |
|---|---|---|---|
| Rubber | | ACME | |
| 12 Anodic Aluminum Oxide | AAO-1 | Synkera Technologies | 13-mm dia., 51-μm thick, pore density $1 \times 10^{11}$ cm$^{-2}$, pore diameter 13 nm |
| 13 Anodic Aluminum Oxide | AAO-2 | | 13-mm dia., 101-μm thick, pore density $1 \times 10^{11}$ cm$^{-2}$, pore diameter 18 nm |
| 14 Zeolite (ZSM-5) | ZSM-5 | Hutong LTD | Rod shape, 3-mm dia., 26-mm long, Si/Al ratio 50 |
| 15 Zeolite (Nay) | Nay | Global Co., | Rod shape, 2.7-mm dia., 26-mm long, Si/Al ratio 50 |

Acrylic sheets were purchased from Signtrade, UAE. Needle, and ball valves, stainless steel (SS) tubes, SS bolts, two-part quick epoxy (Devcon®), and two-part Epo-Putty (ALTECO) were purchased from the local hardware stores. Porous SS discs (3 mm thickness) were purchased from Mott Corp. (USA). Thin epoxy (Epothin®) was purchased from Buehler. Hydrogen (99.9992%), nitrogen (99.9992%), helium (99.9992%), neon (99.985%), argon (99.9992%), carbon dioxide (99.99%), methane (99.999%), ethane (99.5%), ethylene (99.95%), and propane (99.999%) gas cylinders were purchased from Air products (UAE). Considering an experimental setup in accordance with the present invention—the layout of an exemplary six-channel gas permeation system is shown in FIG. 1. Referring back to FIG. 1, the experimental setup of the system 100 can be constructed from the gas reservoir 110 of the pressurized test gas and the gas distribution unit 108 which also acts as the base for the six membrane holders (m1-m6) 102 arranged in such a way to allow simultaneous parallel permeation of the test gas from the pressurized gas reservoir 110 through the membranes 104 into the individual confined spaces 106 behind membranes m1-m6, respectively. The pressures in the confined spaces 106 behind the membranes (i.e., Pm1-Pm6) were recorded by means of six individual pressure sensors (i.e., S1-S6) 114. Referring back to FIGS. 2A and 2B, two different types of membrane holders (i.e., Type I and II) were designed, fabricated, and used throughout the present work. Type-I holders (sandwich-type holder) as already shown and explained in FIG. 2A was used for thin membranes such as PC, PI, T-AF, SR and AAO-1, and AAO-2. Whereas Type-II holders (disc-shaped holder) as already shown and explained in FIG. 2B were used for rod-shaped zeolites.

In an exemplary embodiment, Type I holders or sandwich-type holders were constructed from two acrylic discs (50 mm or 90 mm dia, each), where the membranes were secured in place between two O-rings and supported by a porous SS disc as shown in FIG. 2A. The two acrylic discs were assembled by SS bolts (fastener). In another exemplary embodiment, Type II holders or disc-shaped holders were constructed from a single thick transparent acrylic disc (50-mm dia, 30-mm height). Further, either a single or multi-holes (5-mm dia and 27 mm deep, each) were drilled from one side of the disc. Each hole was filled with thin epoxy and left to gel for approximately two hours then a zeolite rod was inserted in each channel and left overnight for the epoxy to fully cure. Then the cross-sections of the zeolite rods were exposed at both sides by slow stepwise facing (0.5 mm, each) of the holder by CNC machining using a 4-mm end mill.

Figure 2C:
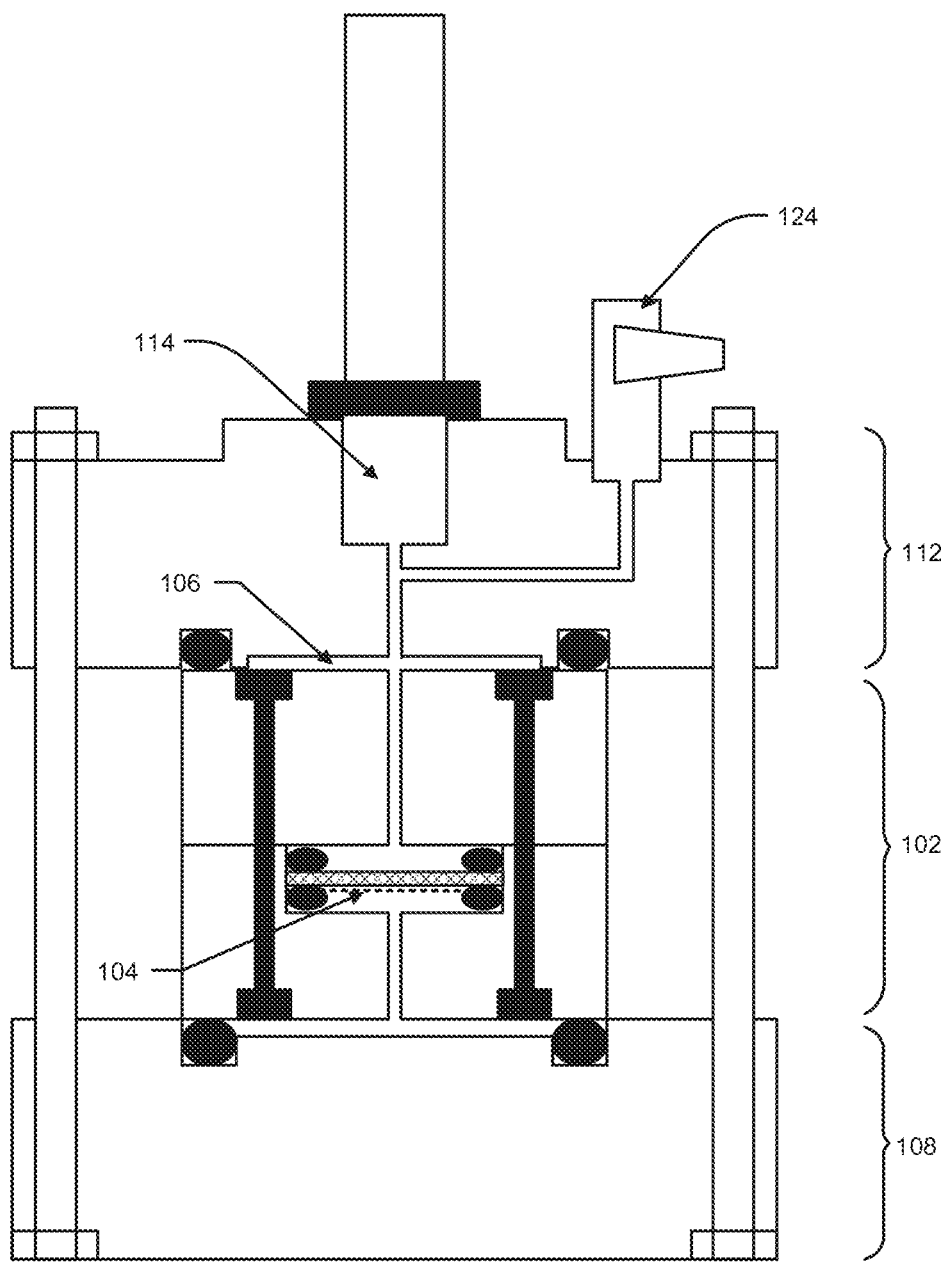
FIG. 2C illustrates an exemplary view of an assembled one channel of the proposed system showing the membrane holder, the confined space, the pressure sensor, the gas vent channel, and the ball valve, in accordance with an embodiment of the present invention.

Referring to FIGS. 1 and 2C, the confined space 106 behind each membrane 104 was created by an acrylic cover disc 112 which also served as a holder for the pressure sensors 114. In an implementation, such cover disc 112 was constructed from a transparent acrylic sheet (30-mm thick). A ¼" NPT thread was machined on the upper side to install the pressure sensor (Ashcroft 0-60 psi with 1-5 VDC output and ¼" NPT male connection). A 2-mm diameter hole was drilled through the disc axis to allow gas access to the pressure sensor 114. Two features were machined in the lower face: (i) the 6-mm O-ring groove and (ii) unless otherwise stated, a 0.5-mm depth central groove to act as a constant volume cavity behind the membrane 104. A horizontal vent line, connecting the pressure sensor compartment and a ball valve 124 was machined as shown in FIG. 2C.

Furthermore, an 8-Channel interface card (118) (Model ADC-20, Pico Technology) along with the PicoLog software was used for data acquisition. The data collected and displayed by this data acquisition system can be either manually analyzed by the user or processed by the computing unit to identify the test gas. A 4-Channel computer-controlled gas mixer (Model MFC-4, Sable Systems, USA) was used to control two Mass Flow Controllers (MFCs) (Sierra Instruments, USA) to prepare gas mixtures of variable compositions. In an implementation, the system 100 was first flushed with the desired test gas to replace air with the test gas inside the entire system 100. Then, the vent valves behind each membrane 104 were closed immediately after flushing. The inlet pressure of the test gas was readjusted to the desired pressure then the test gas was allowed to expand at time zero (by means of the three-way valve) to the gas distribution unit 108. The gas pressure accumulation behind each membrane 104 was measured at a rate of one sample per second. The pressures (Pm1-Pm6) were allowed to proceed for enough time to equilibrate with the pressure of the inlet compartment.

Several aspects were rationalized in constructing the proposed system. These included 6-channel system for rapid testing of up to six membranes, negligible internal total volume compared to that of the gas reservoir, tolerate pressures up to 100 psi, leak tight (<0.1 psi/hour), convenient pressurization, and venting of the test gas into vacuum line for safe gas flushing, convenient membrane replacement, and continuous pressure monitoring with high resolution (0.01 psi). All construction prerequisites were achieved by the proper design of a 6-channel system in which 6 membranes holders were linearly arranged on a rectangular base (cf. FIGS. 1 and 2D). Thick transparent acrylic sheets (20 and 30 mm thick) were used throughout the construction and proved suitable to achieve the required safe pressure rating. The volume of the gas inlet compartment was 1500 cm$^3$ which was significantly larger than the internal volume (approx. 50 cm$^3$) of the connection line and the gas distribution unit. Finally, the careful construction and the proper O-ring sizes successfully led to the desired excellent leak-proof (less than 0.1 psi/hour).

Figure 2D:
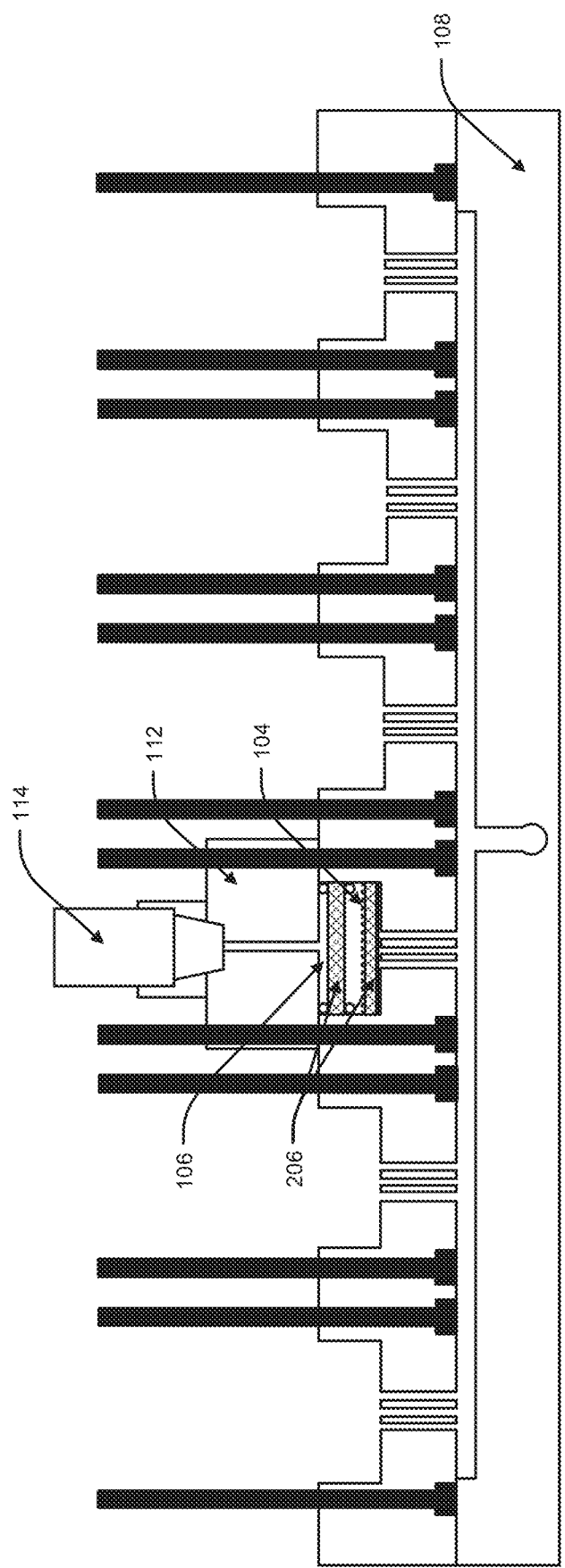
FIG. 2D illustrates an exemplary embodiment of the system, wherein the membrane is installed directly inside respective cylindrical cavities in the gas distribution base, in accordance with an embodiment of the present invention.
Figure 4:
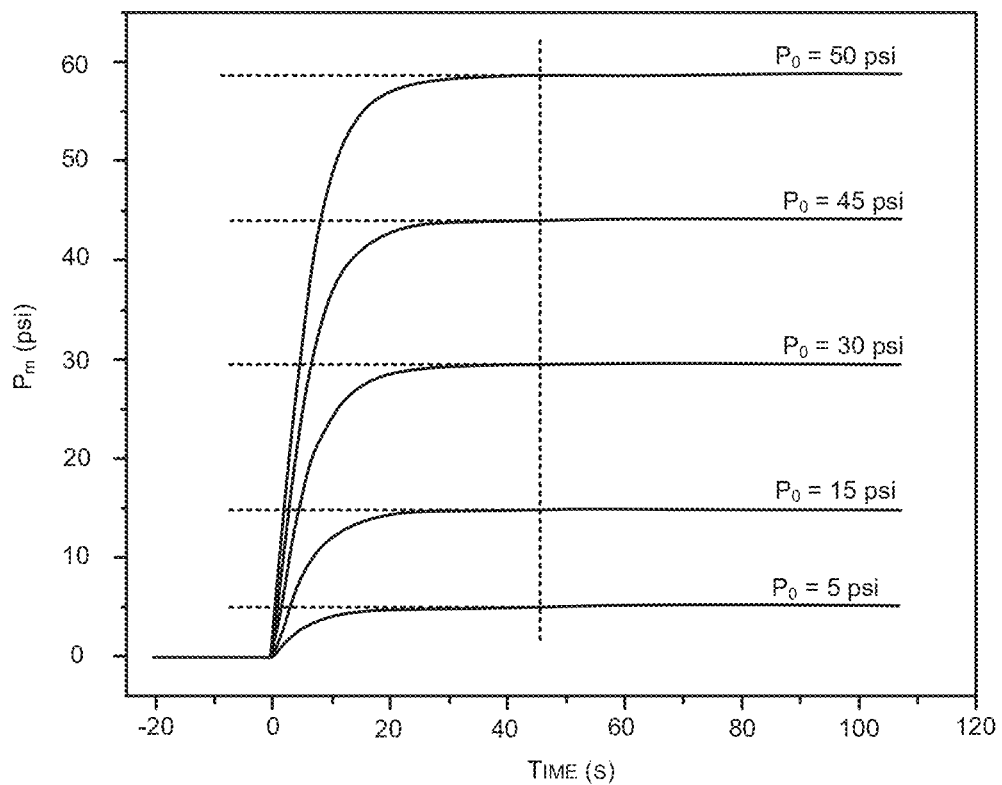
FIG. 4 illustrates a graph depicting the effect of test gas inlet pressure on the rate of accumulation of the pressure (Pm) behind the membrane when $N_2$ is used as test gas and Polycarbonate PC-1) is used as the membrane.

In principle, the system could be designed in such a way to place the membranes 104 directly in cylindrical cavities machined in the base distributer unit 108 as shown in FIG. 2D. However, sealing the membrane 104 in a replaceable membrane holder 102 offered several advantages such as more convenient replacements of the membranes, keeping all channels generic which can accommodate either Type I or Type II holders, and allowing convenient use of membranes of considerably varied thicknesses (6 µm, e.g., with PC-1 membrane and up to 26 mm as with the zeolite rods. Besides the membrane type, which is obviously the most important variable in the present study, three initial variables were rationalized, i.e., temperature, initial inlet pressure ($P_o$) of the test gas, and the volume of the gas inlet compartment. The effect of temperature was not investigated since the system was meant to operate in an air-conditioned lab. Even for possible future outdoor operation under wide temperature variations (e.g., ±20° C.), the changes in gas permeabilities for such small temperature variations should be negligible. However, the effects of the gas inlet pressure and the volume of the inlet gas compartment were studied, respectively. The effect of gas inlet pressure was evaluated using nitrogen as a test gas and PC-1 membrane at five different inlet pressures and the results obtained were presented in FIG. 4. As mentioned previously, $P_m$ rises asymptotically until it equilibrates with the inlet pressure at an intermediate pressure which is slightly smaller than $P_o$ because of the slight expansion of the test gas due to the small internal volume of the gas distribution unit and to the confirmed volumes behind the six membranes. It was noted that the time required for equilibration was independent of the initial inlet pressure. The same behavior was observed when the volume of the inlet compartment was reduced from 1500 to 750 cm³. Such independence of the time required for $P_m$ to reach the maximum equilibrium value from both inlet pressure ($P_o$) and inlet volume ($V_o$), as well as the asymptotic increase of $P_m$ with time, suggested a qualitative analogy between any channel of the present experimental setup and a single RC series electric circuit. This analogy is described in FIG. 5.

The charge (Q) accumulated in a capacitor in an RC series circuit at a time (t) is given by equation [1].

$$Q = CV_b(1 - e^{-t/Rc}) \qquad [1]$$

where $V_b$ is the voltage of the battery; t is the time elapsed since the application of voltage (s); R is the electric resistance (Ohm); C is the capacitance of the capacitor (Farad); RC is the circuit time constant, τ (s); and $CV_b$ is the maximum charge ($Q_{max}$). From equation [1], when t=τ=RC, Q=0.632 $Q_{max}$. Therefore, for a given RC circuit, the charge (Q) accumulated in the capacitor will equal to 63.2% of the maximum charge regardless of the voltage of the battery. Given the proposed analogy, the gas pressure (Pm) in the confined space behind the membrane can be described by equation [2].

$$P_m = P_{max}(1 - e^{-t/R_m C_m}) \qquad [2]$$

Where $P_m$ is the pressure behind the membrane at time t; $P_{max}$ is the maximum pressure behind the membrane which equals to the equilibrium pressure with the inlet compartment; t is the time elapsed since the pressurized test gas in the inlet compartment was released to the base distribution unit; $R_m$ is the membrane resistance to gas transfer; $C_m$ is the volume of the confined compartment behind the membrane, and $R_m C_m$ is the time constant of a given channel, $\tau_m$. The plot of equation [1] for an RC circuit, and the experimental data (shown in FIG. 4 for $P_o$=60 psi) are presented in FIG. 5, respectively, to show the perfect match between both systems. The $R_m C_m$ value (which equals to $\tau_m$) was determined experimentally as the time required for $P_m$ to reach 63.2% of its equilibrium value ($P_{max}$). To verify the assumption of this analogy, the experimental $P_m$ values obtained with the PC-1 membrane and nitrogen as test gas were compared with the calculated $P_m$ values from equation [2] at different t values given that $P_{max}$ is as the equilibration pressure. The result obtained indicated a perfect coincidence between the experimental data and the calculated values which provided sufficient grounds for the validity of the proposed analogy as well as the proposed system.

Figure 5:
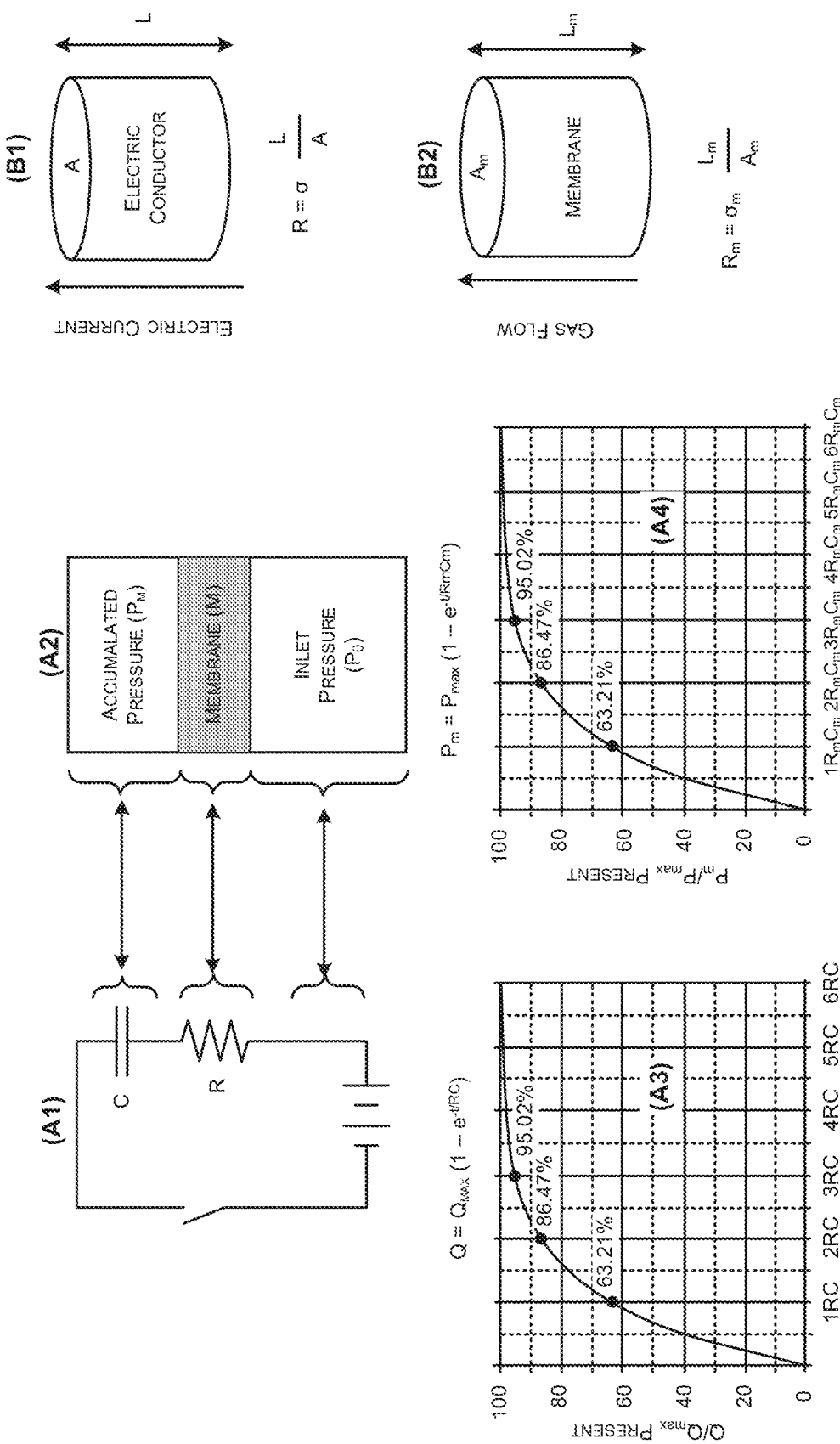
FIG. 5 illustrates an analogy between a single series RC circuit (A1) and any channel of the proposed system (A2), wherein the identical rate of charge (Q) accumulation in the capacitor in the RC circuit and the pressure accumulation (Pm) are shown in (A3) and (A4), respectively, and the analogy between the electric resistor and the membrane is shown in (B1) and (B2), respectively.

In addition to the proposed analogy between the RC series circuit and each channel of the experimental setup, another analogy was envisioned between the membrane resistance ($R_m$) and the resistance (R) of an electric resistor as shown in FIG. 5. Therefore, $R_m$ could also be defined in terms of the membrane thickness ($L_m$), its cross-section area ($A_m$), and its specific resistance ($\sigma_m$). Interestingly, the RC analogy explained nicely the preliminary observations presented in FIG. 4 since the charging time (i.e., the time required for $P_m$ to reach the maximum equilibrium value) is dictated only by the time constant value ($\tau_m$) which equals to $R_m C_m$ and hence is independent of the initial pressure ($P_o$) and the initial volume (Vo) of the inlet compartment.

To further validate the proposed analogy between any individual channel of the gas diffusion system and the RC circuit, the analogy of the volume of the confined space behind the membrane ($C_m$) and the Capacitance of the capacitor (C), a series of pressure sensor holders were machined with different depths to create circular grooves of different volumes and used to monitor $P_m$ using nitrogen gas permeation through identical PI-1 membranes. The obtained $\tau_m$ values were plotted against the volume of the confined circular groove. The excellent linear regression obtained between $\tau_m$ and $C_m$ is the final presented evidence for the validity of the proposed analogy between the experimental system and the RC series circuit. Also, the RC model was adopted in the analysis of facilitated transport in solid membranes with fixed site carriers.

Having confirmed the validity of the overall analogy between the RC circuit and any channel of the present gas permeation setup, the next logical step was to validate the analogy between the membrane resistance ($R_m$) to gas transfer and the resistance (R) to electric current, depicted in FIG. 5. Considering the validation of the analogy between membrane resistance (Rm) and electric resistance (R), the rationale behind this analogy is two-fold. Firstly, to further confirm the validity of the proposed analogy with the RC series circuit model, and secondly to allow a more detailed understanding of the impact of different membrane characteristics such as its thickness, active area, etc. on the experimental results.

Assuming the membrane resistance (Rm) is given by equation [3].

$$R_m = \sigma_m \frac{L_m}{A_m} \qquad [3]$$

and the definition of $\tau_m$ which is conveniently measured experimentally:

$$\tau m = R_m C_m \qquad [4]$$

Substitute from [3] in [4] for $R_m$ $$\tau_m = \sigma_m \frac{L_m}{A_m} C_m \quad [5]$$

The validation of equation [5] is experimentally feasible by determining $\tau_m$ values for a given variable (e.g., membrane thickness, $L_m$) while keeping the other variables constant. For given intrinsic membrane properties which affect $\sigma_m$ and at constant $A_m$ and $C_m$, equation [5] is reduced to equation [6].

$$\tau_m \alpha L_m \quad [6]$$

Therefore, one should expect that the experimentally measured time constant ($\tau_m$) values are directly proportional to the membrane thickness ($L_m$). It must be noted that $L_m$ should be the length through which the gas permeates through the membrane. This length can vary significantly with membrane tortuosity but in all cases, it should be proportional to the geometric thickness of the membrane ($L_m$).

Figure 6A:
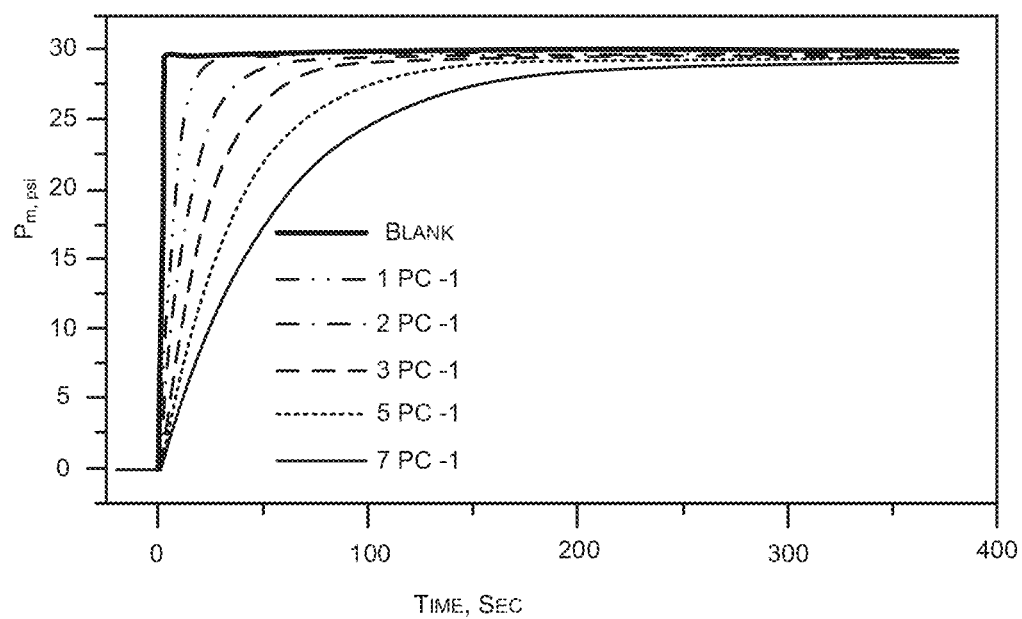
FIGS. 6A-6C illustrates exemplary graphs depicting the effect of the number of stacked PC-1 membranes (A), length of ZSM-5 rods (B), and the total area of ZSM-5 (expressed as the number of ZSM-5 rods) (C), respectively, on the membrane time constant ($\tau_m$).
Figure 6B:
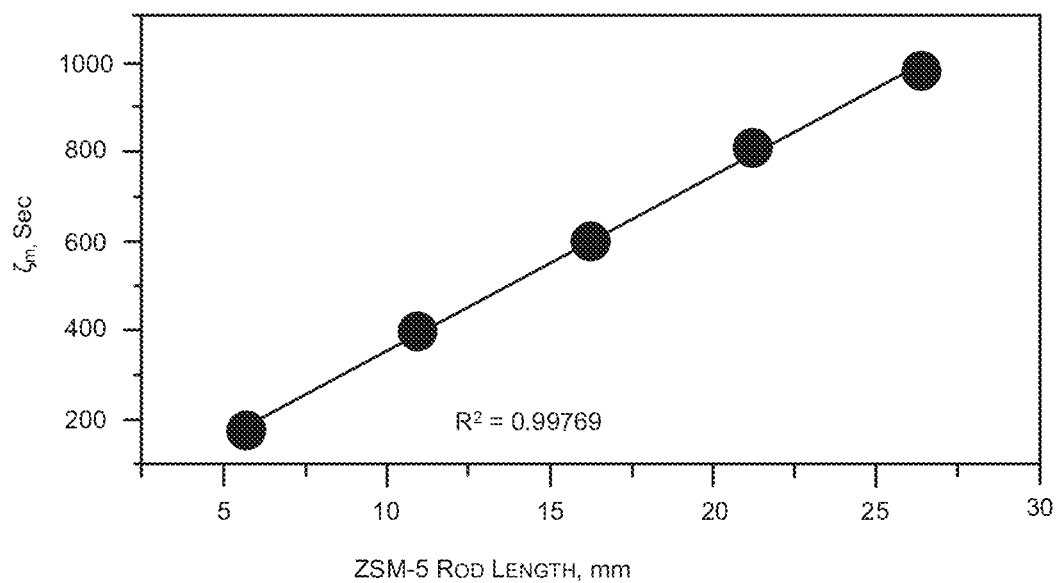
Figure 6C:
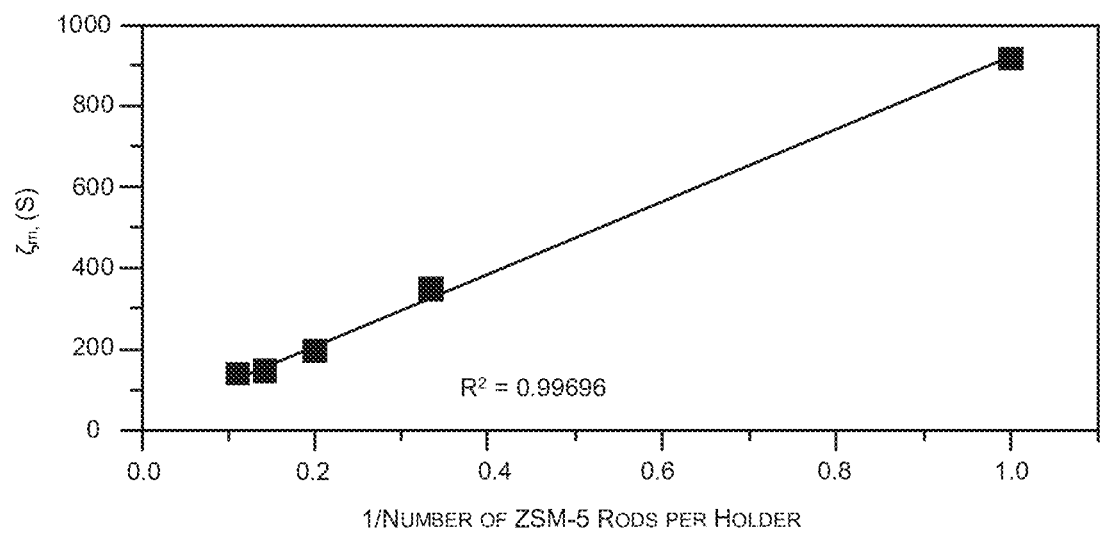

Equation [6] was verified by PC-1 membranes and Zeolite rods, respectively. First, 1, 2, 3, 5 and 7 PC-1 membranes were stacked in 5 membrane holders, respectively, and tested simultaneously. It was assumed that the overall membrane thickness is a sum of the individual stacked membranes. The results obtained were presented in FIG. 6A. The membrane time constant ($\tau_m$) values were determined at 63.2% of the final equilibrium pressure value and plotted against the number of membranes. The excellent linear regression ($R^2=0.99923$) is shown in the insert of FIG. 6A agrees perfectly with the prediction of Equation [6]. This conclusion was confirmed further using Zeolite ZSM-5 rods of different lengths installed in Type-II holders, respectively. The impressive linearity was obtained between the measured ($\tau_m$) and the rod length (presented in FIG. 6B) not only confirmed the analogy but also confirmed the safe generalization of this conclusion to different types of membranes.

For a given membrane type and thickness and $C_m$, Equation [5] is reduced to equation [7]:

$$\tau_m \alpha \left( \frac{1}{A_m} \right) \quad [7]$$

To demonstrate such direct dependence of $\tau_m$ on $1/A_m$, a series of ZSM-5 membrane holders were prepared with 1, 3, 5, 7 and 9 parallel rods, respectively, to have a series of membrane holders of identical length (i.e., 22.0 mm) and different total cross-section areas. The corresponding $\tau_m$ values were determined using nitrogen. The results obtained were presented in FIG. 6C. It is evident that $\tau_m$ increases linearly with (1/number of ZSM-5 rods), which is proportional to the total active area ($A_m$). The excellent linear regression confirmed the validity of equation [7] which is completely analogous to $R \alpha (1/A)$ as depicted in FIG. 5.

For constant geometric parameters, i.e., $L_m$, $A_m$, and $C_m$, Equation [5] is reduced to equation [8]:

$$\tau_m \alpha \sigma_m \quad [8]$$

Despite the role of the membrane geometric parameters (i.e., thickness and area) in determining the overall membrane resistance ($R_m$), the membrane specific resistance (resistivity, $\sigma_m$) remains the most essential parameter which is in turn strongly dependent on several factors such as membrane material, membrane surface treatment, pore size, pore density, etc. To complete the study of the proposed $R_m$ and R analogy, other experiments were conducted using membranes of identical geometric parameters but differ in one intrinsic property such as membrane surface treatment and pore density. In contrary to $\sigma$ which is only determined by the intrinsic properties of the electric conductor, $\sigma_m$ is also sensitive (albeit to different extents) to the permeating gas as will be described later. Actually, the sensitivity of $\sigma_m$ to the gas type forms one of the essential bases of the hypothesis of the present work. In conclusion, the analogy between $R_m$ and R has been fully validated using each of the relevant variables, i.e., the length, cross-section, and resistivity as depicted in the FIG. 5.

Figure 7A:
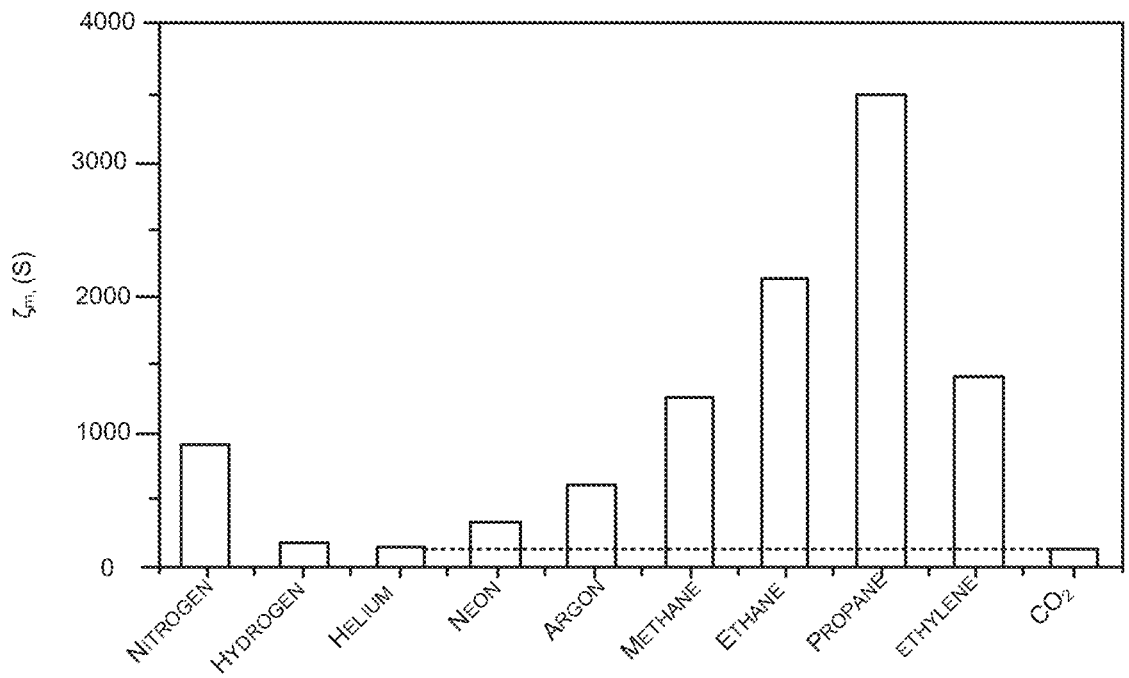
FIGS. 7A-7C illustrates an exemplary graph depicting time constants ($\tau_m$) obtained for the test gases using T-AF (A), SR (B), and ZSM-5 (C), respectively.
Figure 7B:
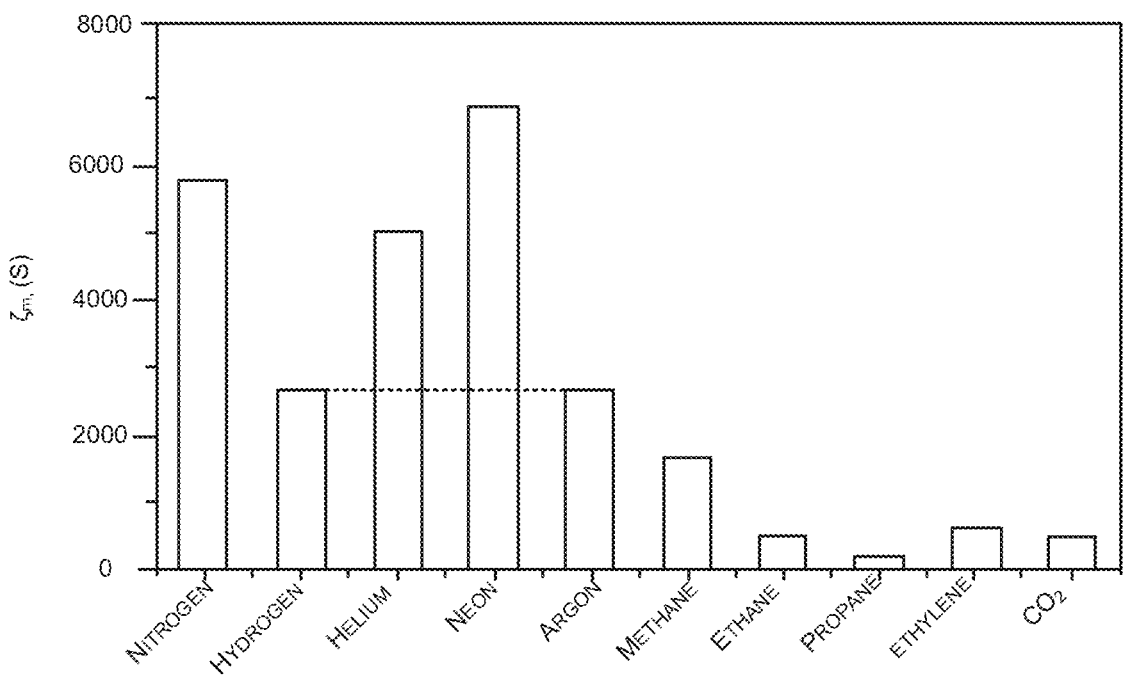
Figure 7C:
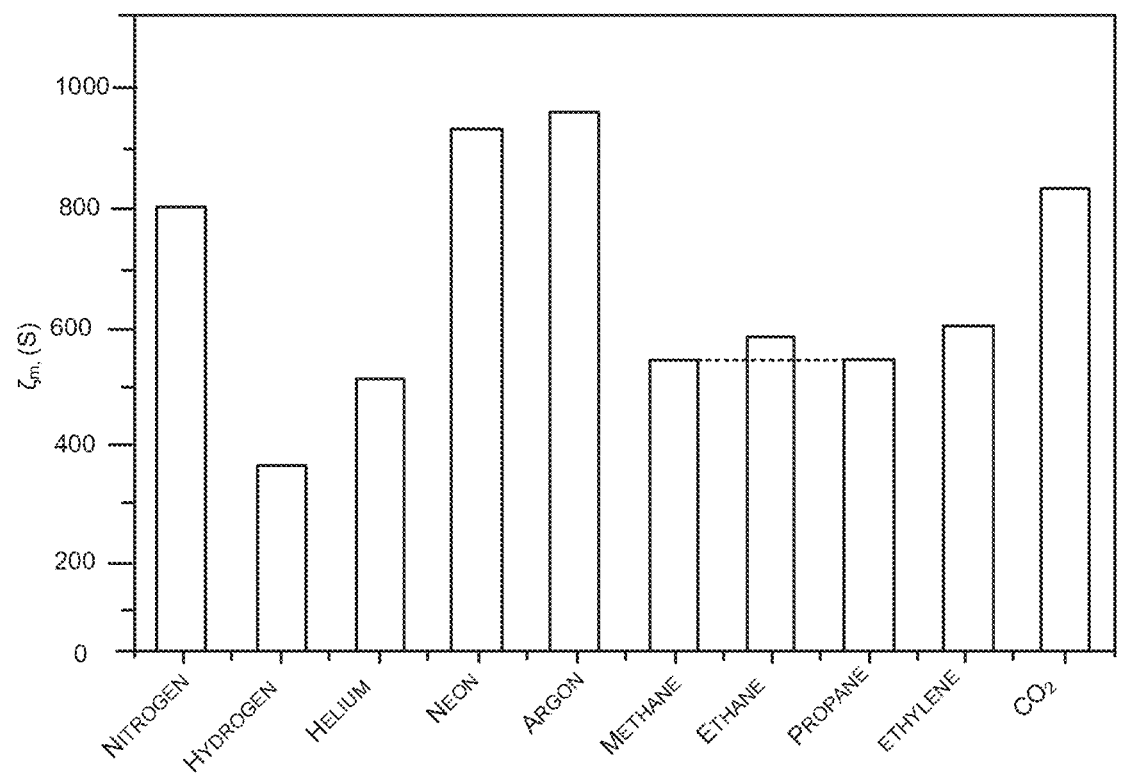

Considering the fingerprinting of test gas, the gas-permeable membranes to be employed in the present work must exhibit differential permeation rates for the test gases. Membranes that exhibited identical permeation rates to all gases (e.g., PEEK-20 and PVDF-20) were excluded since their contribution to the gas identification will be nil. In principle, a single membrane could be used in identifying individual gases based on their specific permeation rates. However, it is not expected that a single membrane can be reliable since it is very likely to have two or more gases exhibiting similar or very close permeation rates which would hinder their accurate identification. This prediction is experimentally demonstrated as shown in FIGS. 7A to 7C for the permeation of the ten test gases through T-AF, SR, and ZSM-5 membranes, respectively. Although each membrane exhibited considerable differences in the permeation rates for the test gases, the high risk of getting very close similarity (i.e., greater than 99%) was evident even within such a relatively small gas database (i.e., the ten test gases used in the present work). For example, such close similarity was observed for helium and $CO_2$ using F-AF (FIG. 7A), hydrogen and argon using SR (FIG. 7B), and methane and propane using ZSM-5 (FIG. 7C). Normally, this risk will increase with the size of the gas database. Similar to the arrays of sensors used in the construction of electronic noses and tongues, an array of different parallel membranes could exhibit patterns of permeation rates that are more characteristic fingerprints for the test gases.

As one might anticipate, the different the nature of the membranes (and hence the permeation mechanisms through them) the higher the overall selectivity of the pattern output from the membrane array. For example, failing to precisely discriminate between helium and $CO_2$ using T-AF membrane channel (FIG. 7A), can be easily supplemented by the channels equipped with SR or ZSM-5, respectively (cf. FIGS. 7B and 7C). In addition to the three membranes presented in FIGS. 7A-7C, six more membranes exhibited the required differences in the permeation rates for the test gases.

Figure 8:
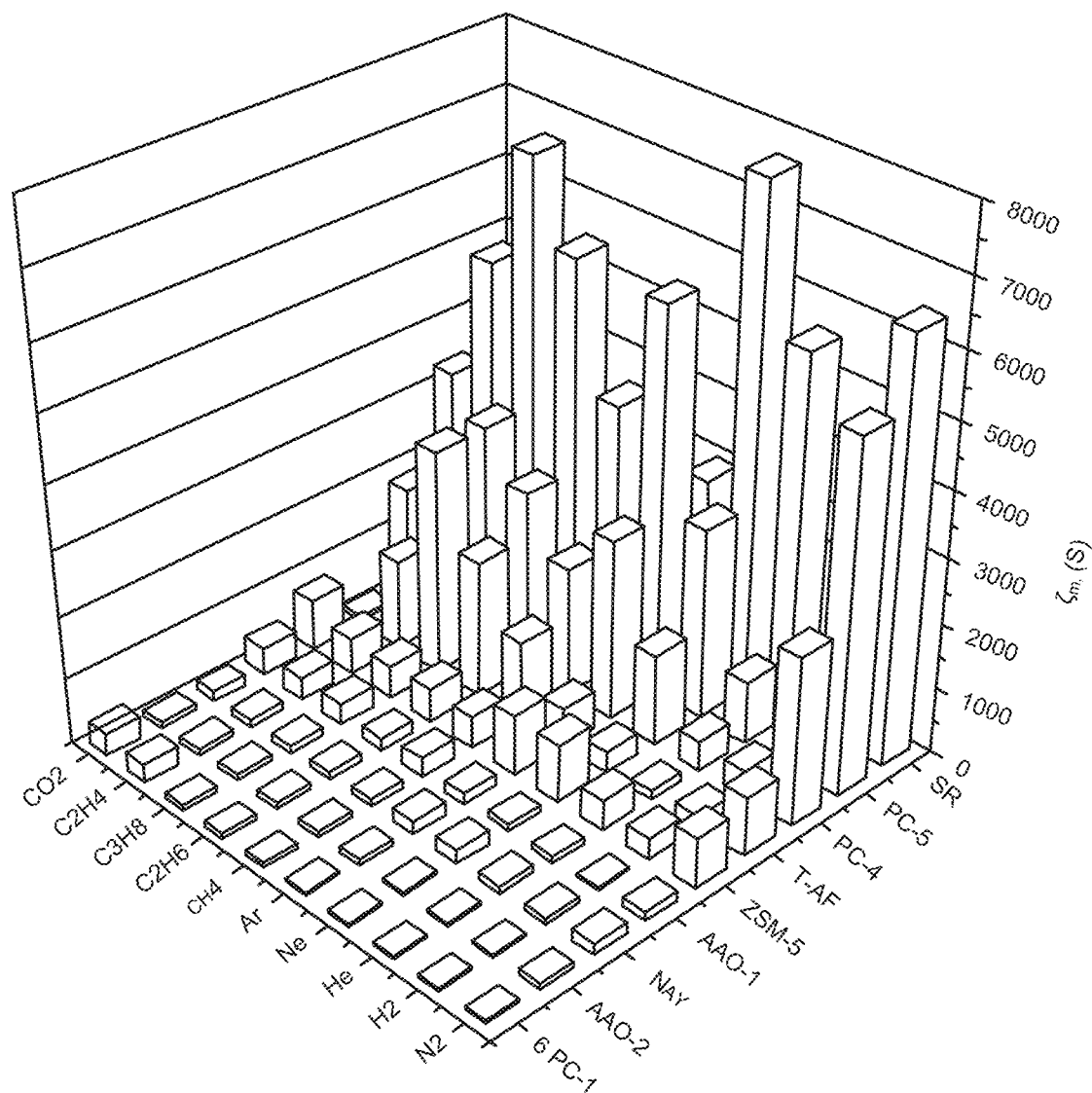
FIG. 8 illustrates an exemplary 3D-bar graph showing the characteristic permeation patterns (fingerprints) obtained for the test gases using 9 different membranes.

The $\tau_m$ values for all test gases obtained with different membranes were plotted in FIG. 8. The nine $\tau_m$ values obtained for a given test gas through the 9 membranes, constituted the permeation pattern proposed in this work as a novel approach to get a characteristic fingerprint for a test gas. The apparent low ability of six layers of PC-1 (abbreviated as 6PC-1), AAO-2, Nay, AAO-1, and ZSM-5 membranes to show appreciably different $\tau_m$ values for the test gases is attributed to the compressed scale used to plot all the $\tau_m$ values which vary considerably with the membrane type. Fast permeation through a given membrane results in small $\tau_m$ values and vice versa for slow permeating membranes.

Figure 9A:
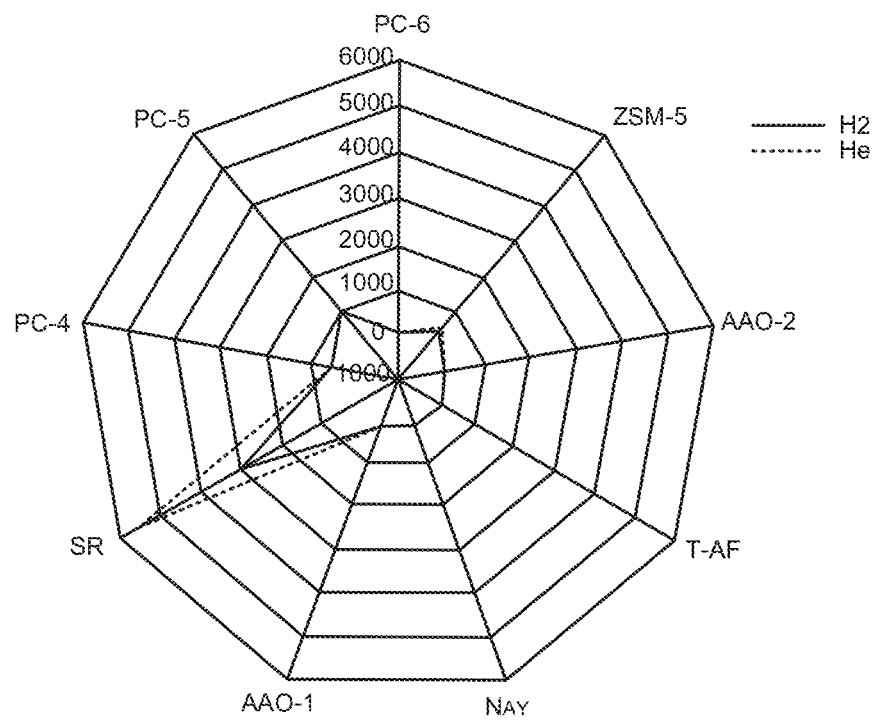
FIGS. 9A-9E illustrates exemplary Radar plots showing the sensitivity of the present system to discriminate between the lightest two gases (A), noble gases (B), methane, ethane and propane (C), argon, propane and carbon dioxide which have comparable molar masses (D), and ethane and ethylene (E), respectively.
Figure 9B:
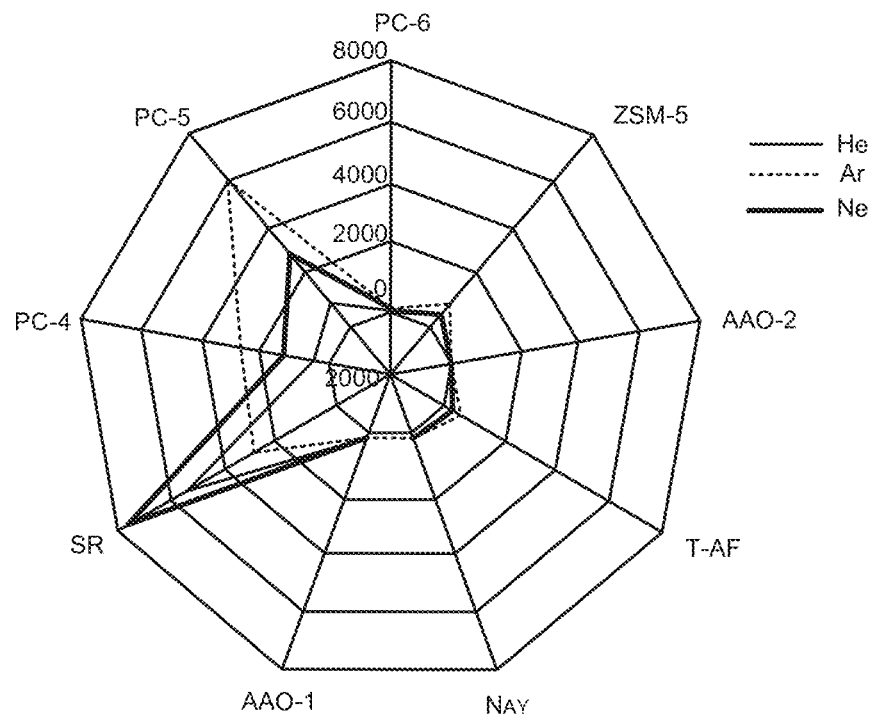
Figure 9C:
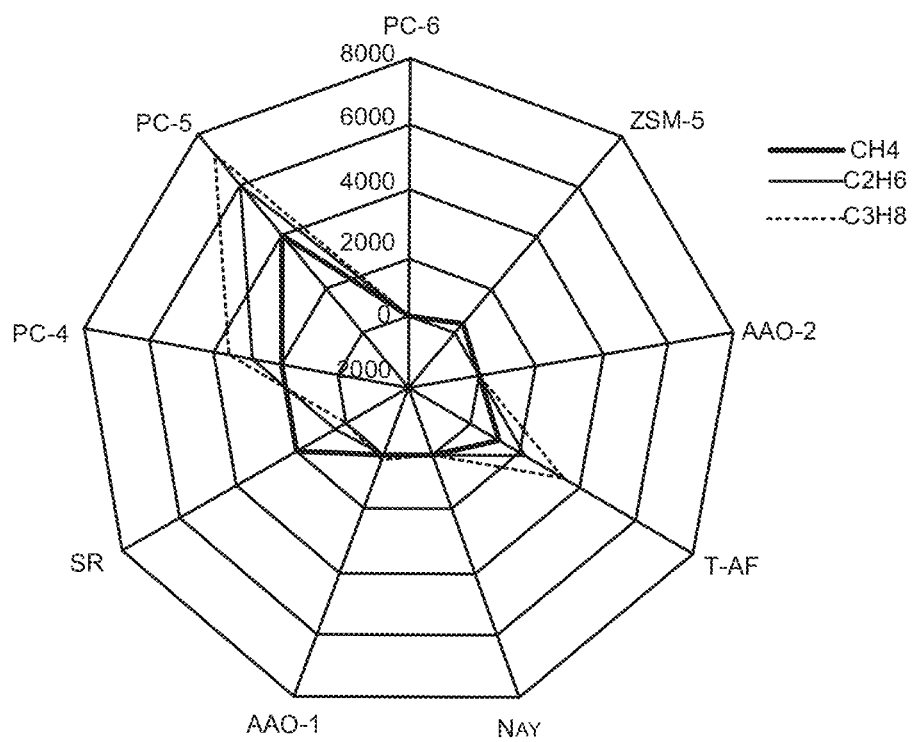
Figure 9D:
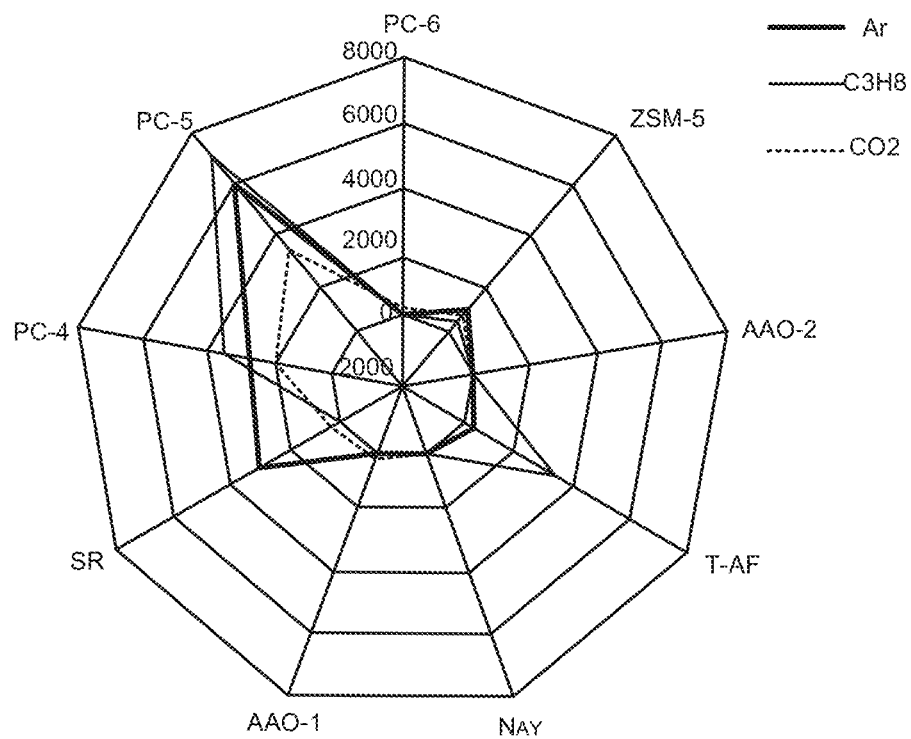
Figure 9E:
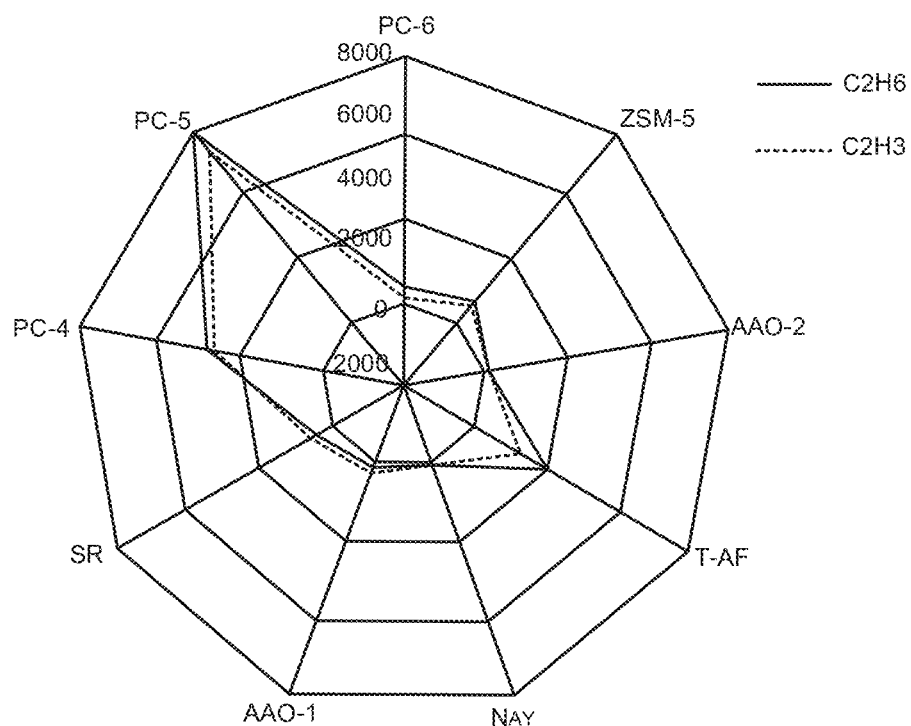
Figure 9F:
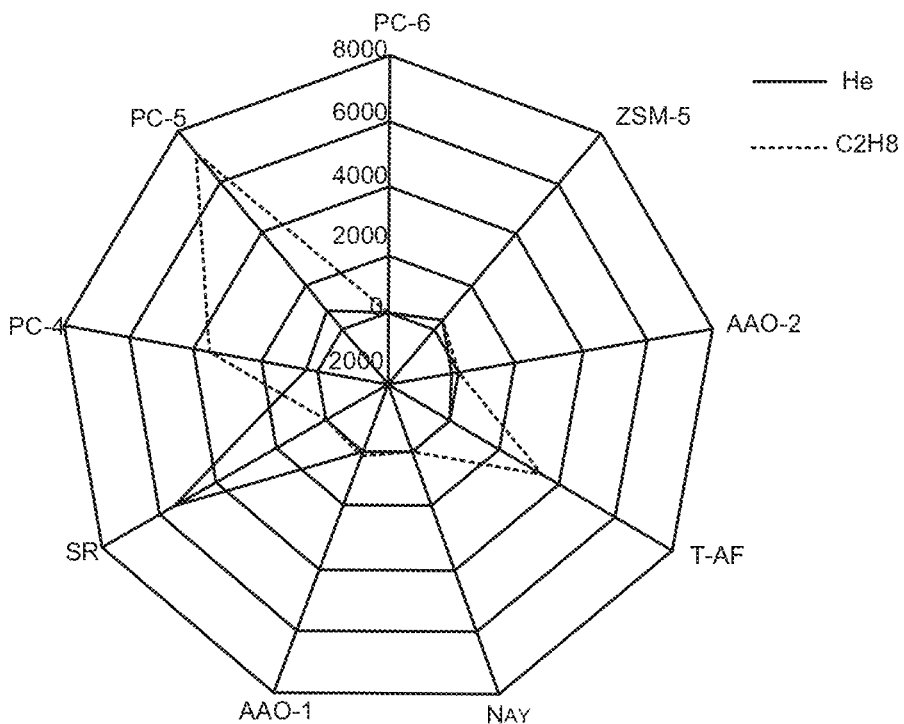
FIG. 9F illustrates the substantially different fingerprints of helium and propane (F).

Based on the results presented in FIG. 8, it is evident that the selected nine membranes (channel no. 1 to 9, albeit tested in two runs using the present 6-channel system) can offer a set of nine different values for each gas. The anticipated high selectivity (presented collectively in FIG. 8 as a 3D bar graph) is presented in FIGS. 9A-9F to show the characteristic fingerprints of closely related gases in the form of Radar plots for more convenient visual recognition of the gas fingerprint as an area enclosed by the graph showing $\tau_m$ values obtained with the nine different membranes. These include hydrogen and helium (FIG. 9A), monoatomic noble gases (FIG. 9B), homologous series of hydrocarbons (FIG. 9C), gases of comparable molecular weights (FIG. 9D), a paraffine and its corresponding olefin (FIG. 9E). It is evident that even with any of the close relations presented in FIGS. 9A-9E in such compressed scales, there are multiple differences identified by visual inspection in each case. As one might expect, the permeation patterns should become much more distinct for comparing the fingerprints of gases that are less chemically related such as helium and propane (FIG. 9F). The success of the obtained permeation patterns for gas fingerprinting is evident in FIGS. 9A-9F since no two gases exhibited identical permeation patterns.

It would be obvious for a person skilled in the art that although not elaborated in the present disclosure, it is also reasonable to assume that the test gas is not necessarily in the form of pure gas. A gas mixture, e.g., crude sour natural gas with percentile levels of $CO_2$ and $H_2S$ is expected to have a different fingerprint after the removal of the acid gases. The reproducibility for all membranes was also critically assessed. The results obtained revealed superior precision. The coefficient of variation (CV) for three measurements varied from 0.31% (for AAO-1) to 0.75% (for SR membrane). Such high precision is essential to ensure high sensitivity to differentiate between closely related gases.

According to Equation 5, $t_m$ values obtained with a given membrane can be either decreased or increased while retaining the relative time constants for all gases which is primarily dictated by the membrane resistivity ($\sigma_m$). The membrane time constant values ($\tau_m$) can be manipulated in such a way to have comparable values among the selected membranes and to keep them with relatively short times for rapid testing. This can be achieved by changing the geometric variables, i.e., membrane area, membrane thickness, and the volume of the confined space behind the membrane. The membrane time constant $\tau_m$ was used in the present work because of its analogy with the electrical RC series circuits but the relative time constants should be kept at shorter times, e.g., the time required to reach 20% or 50% of the $P_{max}$ and not necessarily the time required to reach 63.2% of $P_{max}$. This is confirmed by plotting the normalized $\tau_m$ values measured at $P_m$ equals to 0.2, 0.5, and 0.63 $P_{max}$. This finding is especially important for dense membranes (e.g., SR and T-AF) which exhibit low permeabilities (large $\tau_m$ values) since the $P_m$ values can be measured at substantially smaller fractions of $P_{max}$ without compromising the membrane contribution to the gas identification.

Figure 10A:
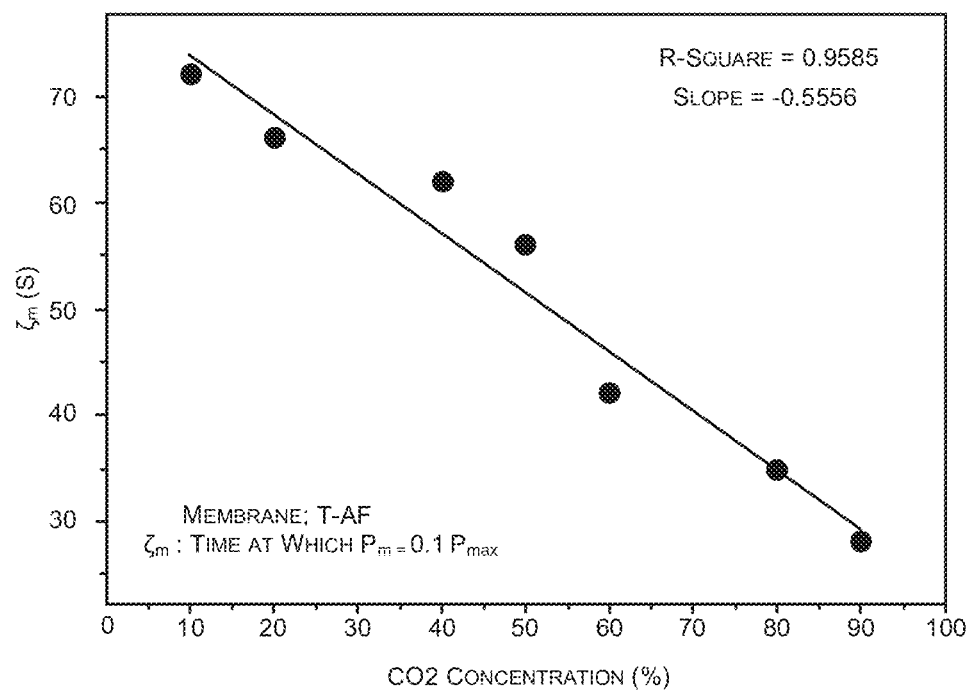
FIG. 10A-10C illustrates exemplary graphs depicting linear dependence of $\tau_m$ observed for $CO_2$—$N_2$ mixtures on $CO_2$ concentration obtained with T-AF (A), PC-5 (B), and SR (C), respectively.
Figure 10B:
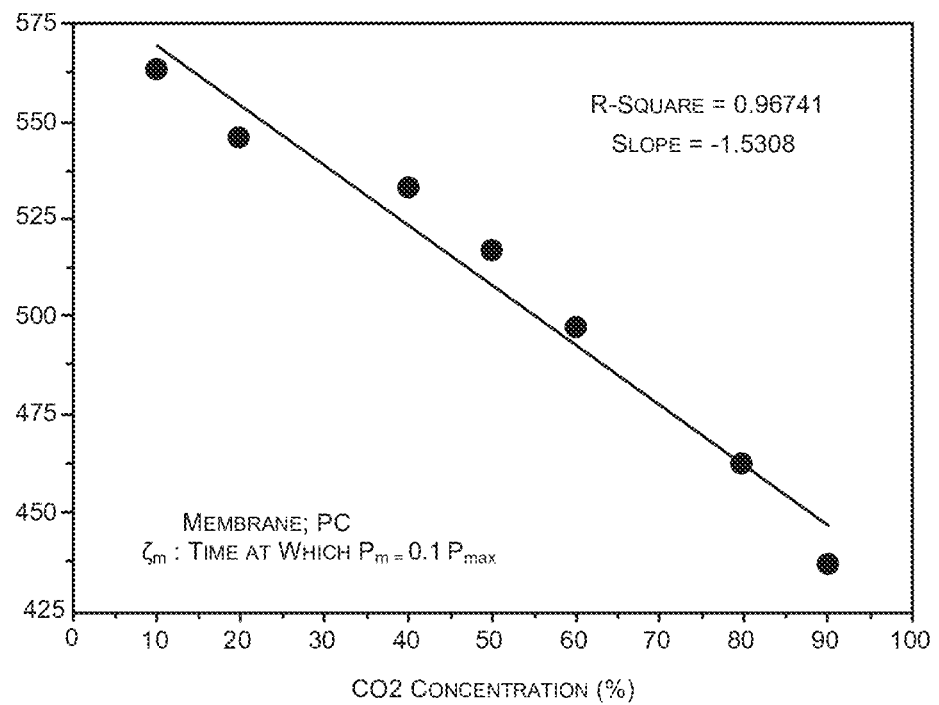
Figure 10C:
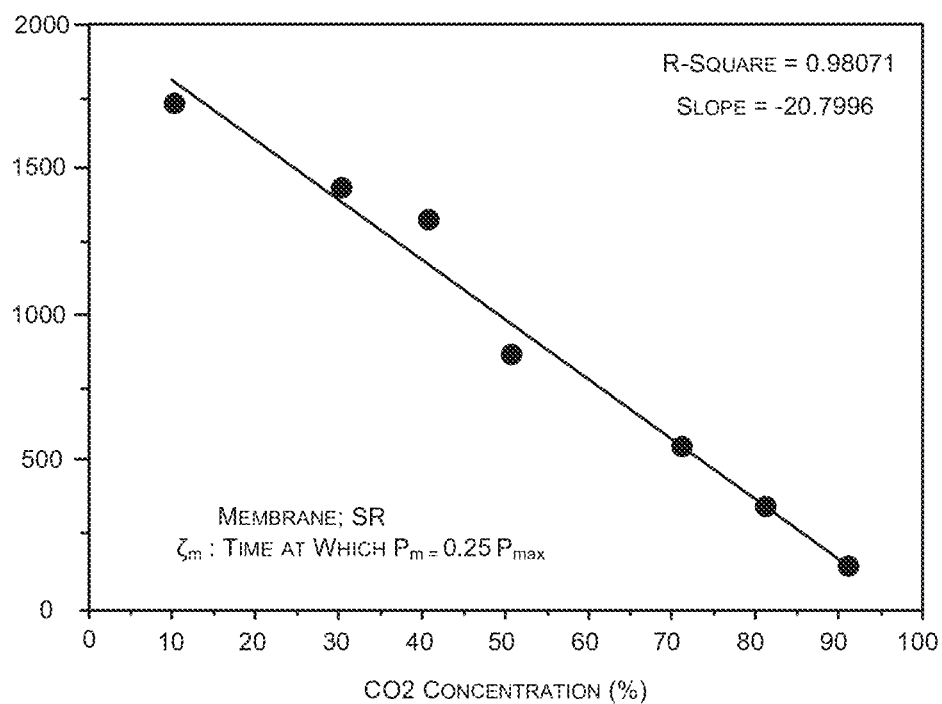
Figure 10D:
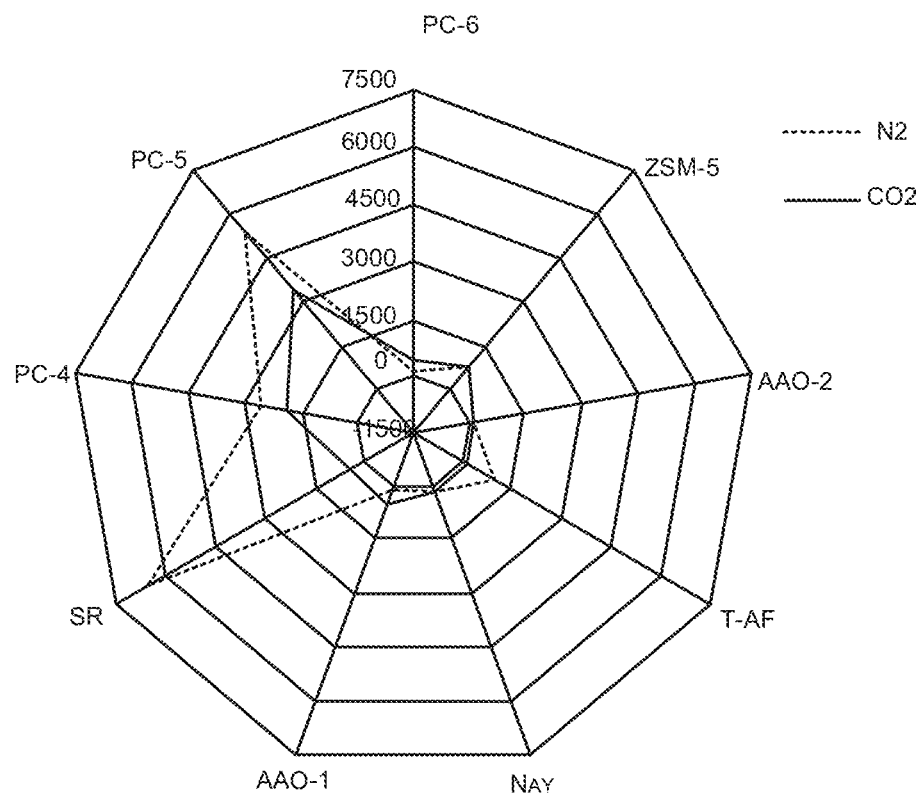
FIG. 10D illustrates a Radar plot depicting the sensitivity obtained with each membrane being determined by the corresponding ratio of $N_2/CO_2$ permeability.

Considering a semi-quantitative analysis of $CO_2$—$N_2$ gas mixture, at least one channel of the proposed system was used to perform a semi-quantitative analysis of binary gas mixtures. The membrane of choice was taken as a membrane that exhibits the highest ratio between the $t_m$ values for the two individual gases constituting the binary mixture. Zeolite ZSM-5 membrane, for example, will not be a suitable option for $CO_2$ and $N_2$ binary mixtures since the two gases have almost identical permeation rates. Whereas T-AF, PC-5, and SR membranes exhibited $\tau_m$ values sensitive to $CO_2$ concentration in its mixture with $N_2$. The relative sensitivities (measured as the slope of the calibration plot) obtained with T-AF, PC-5, and SR were 1, 2.75, 37.4, respectively, which were attributed to the relative $\tau_m$ values with these membranes as shown in FIGS. 10A-10D. FIGS. 10A-10C illustrates exemplary graphs depicting linear dependence of $\tau_m$ observed for $CO_2$—$N_2$ mixtures on $CO_2$ concentration obtained with T-AF (A), PC-5 (B), and SR (C), respectively. FIG. 10D illustrates a Radar plot depicting the sensitivity obtained with each membrane being determined by the corresponding ratio of $N_2/CO_2$ permeability.

Those skilled in the art would appreciate that the present invention allowed a full understanding of the involved variables in the proposed system and the experimental setup, which paved the road to a miniaturized and portable version of the system taking advantage of the following findings (i) neither the inlet pressure nor the volume of the inlet compartment has an effect on $\tau_m$ and hence the same results can be obtained with a lighter and smaller system and the needed pressurization could be achieved by a syringe for the test gas injection into a small inlet compartment, (ii) the pressure sensors could be replaced with micro and wireless sensors to allow the construction of a portable system, (iii) the number of membranes can be limited to the most discriminating 4 or 5 membranes which could further help in the system miniaturization as needed, and (iv) the construction can be further simplified by employing a single cover which holds the needed 4-5 micro pressure sensors. Thus, the present invention provides an improved, and efficient approach for gas identification/fingerprinting for the construction of portable and reliable electronic noses, which allows identification, in principle, of any gas or gas mixtures and is also able to discriminate between closely related gases. Besides, the non-requirement of temperature and moisture-sensitive chemical-based gas sensors in the present invention, makes it reliable, robust, and less prone to failure. The present invention can be simplified by employing micro and wireless sensors, along with a single cover that can hold the needed 4-5 sensors in the confined spaces behind the membranes. This can enable the construction of portable and reliable electronic noses.

It is also to be appreciated by a person skilled in the art that while various embodiments and figures of the present disclosure have elaborated the involvement of six holders, membranes, cover disc, and pressure sensors, however, the number of components of the present invention is not just limited to six and can be of any number based on the requirement, and all such embodiments are also well within the scope of the present disclosure. Further, while various embodiments and figures of the present disclosure have elaborated upon the use of a computing device for processing the data collected by the sensors for gas identification (fingerprinting), however, the sensor data can also be manually analyzed or processed by a user or skilled person for gas identification, and all such embodiments are well within the scope of the present disclosure. Furthermore, while various embodiments and examples in the present disclosure have elaborated upon identifying specific test gases (helium, argon, hydrogen, nitrogen, carbon dioxide, methane, ethane, propane, and ethylene) using a set of specific membranes (Teflon AF®, Silicone Rubber, track-etch hydrophilic polycarbonate, track-etch hydrophobic polycarbonate, track-etch polyimide, nanoporous anodic aluminum oxide, Zeolite ZSM-5, and Zeolite Nay), however, any other membrane can also be used and the present invention is capable of identifying any gas without any limitation, and all such embodiments are well within the scope of the present disclosure. As used herein, and unless the context dictates otherwise, the term "coupled to" is intended to include both direct coupling (in which two elements are coupled to each other or in contact with each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary device.

Moreover, in interpreting the specification, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The present invention enables simultaneous identification of multiple gases or a composition of a gas mixture. The present invention simultaneously identifies test gas or a gas mixture comprising any or a combination of helium, argon, hydrogen, nitrogen, carbon dioxide, methane, ethane, propane, and ethylene. The present invention provides a gas identification approach that is also able to discriminate between closely related gases such as ethane and ethylene or carbon dioxide and propane, and the likes, which have almost identical molecular masses. The present invention provides a gas identification approach that does not require moisture and temperature-sensitive gas sensors. The present invention provides a gas identification approach that identifies multiple gases or a composition of a gas mixture based on the simultaneous permeation rate of a pressurized test gas through distinct gas permeable membranes, which requires only a simple pressure sensor. The present invention provides an improved, and efficient approach for gas identification/fingerprinting for the construction of portable and reliable electronic noses. The present invention provides an improved, and efficient system and method for simultaneous identification of multiple gases or gas mixtures based on simultaneous permeation rate of a pressurized test gas through distinct gas permeable membranes, which is also able to discriminate between closely related gases.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A system for identification of a test gas, the system comprising:
    a plurality of parallelly configured holders, each comprising a distinct gas permeable membrane removably disposed therein such that the membranes are configured parallelly, and a confined space is created downstream of each of the membranes;
    wherein the system is configured to enable a simultaneous flow of the test gas through the membranes of each of the holders, which results in permeation of at least a volume of the supplied test gas through the respective membranes, thereby causing accumulation of the permeated test gas in the confined spaces downstream of the respective membranes; and
    a pressure sensor configured in the confined space downstream of each of the membranes, wherein the pressure sensors are configured to monitor rates of accumulation of pressurized test gas in the corresponding confined spaces, and correspondingly generate a first set of signals indicative of the permeation rates or the pattern of permeation of the test gas through the distinct gas permeable membranes, which facilitates in the identification of the test gas based on the simultaneous permeation rates or pattern of permeation of the pressurized test gas through the distinct and respective gas permeable membranes, and
    a reference database comprising a set of known reference gases, wherein the generated first set of signals indicative of the permeation rates or the pattern of permeation of the test gas through the distinct gas permeable membranes is compared to the set of stored patterns of known reference gases in the reference database, for identification of the test gas.

2. The system as claimed in claim 1, wherein the system comprises a gas reservoir configured to store the test gas at a predefined pressure, and wherein the gas reservoir is fluidically coupled to the plurality of holders and configured to enable the simultaneous flow of the stored test gas through the membranes of each of the holders.

3. The system as claimed in claim 2, wherein the plurality of holders is arranged on and fluidically coupled to a gas distribution unit, such that the gas distribution unit allows the simultaneous parallel flow of the test gas, from the gas reservoir, into the membranes.

4. The system as claimed in claim 3, wherein the plurality of holders is fluidically coupled to the gas reservoir and the gas distribution unit through a set of conduits and a two-way valve.

5. The system as claimed in claim 4, wherein each of the pressure sensors is in communication with a computing device that is configured to receive the first set of signals from the pressure sensor and correspondingly extract and display a data pertaining to the permeation rate of the test gas through the corresponding membrane, and wherein analysis is performed on the data, by a user or the computing unit, to determine the one or more characteristics of the test gas.

6. The system as claimed in claim 5, wherein the computing device or the user controls:
    an input valve to enable inflow of the test gas within the gas reservoir, through an inlet of the gas reservoir, to maintain the predefined pressure within the gas reservoir;
    the two-way valve to enable the outflow of the test gas from an outlet of the gas reservoir into the plurality of holders; and
    the ball valve to enable venting of the accumulated gas out of the holders and the system.

7. The system as claimed in claim 3, wherein the volume of the gas reservoir is greater than the total internal volume of the plurality of holders and the gas distribution unit combined.

8. The system as claimed in claim 1, wherein the system comprises a plurality of cover discs, each made of a transparent acrylic sheet and being configured with a respective holder to create a confined space downstream of each membrane.

9. The system as claimed in claim 8, wherein each cover disc is configured to accommodate the pressure sensor thereon and allow accumulation of the permeated gas in the corresponding spaces downstream of the membranes.

10. The system as claimed in claim 8, wherein the system comprises an O-ring positioned in between each of the holders and the corresponding cover disc to restrict leakage of the test gas therefrom.

11. The system as claimed in claim 8, wherein the system comprises a ball valve, the ball valve fluidically connected to each of the cover discs through a conduit, the ball valve configured to facilitate controlled outflow of the test gas or air from the system.

12. The system as claimed in claim 1, wherein at least one of the plurality of holders is a sandwich-type holder comprising a first disc having a first channel, and a second disc having a second channel, such that when adjacent surfaces of the first disc and the second disc are connected to form the sandwich-type holder, a cavity is created between the first disc and the second disc, with the first channel and the second channel fluidically connected to the created cavity.

13. The system as claimed in claim 12, wherein the sandwich-type holder comprises a porous supporting disc configured within the cavity and oriented parallel to the adjacent connected surfaces of the first disc and second disc, wherein the porous supporting disc is configured to hold the membrane within the cavity of the sandwich-type holder.

14. The system as claimed in claim 13, wherein the first disc and second disc are coaxially coupled to each other through a set of fasteners such that the first channel and the second channel are in line and fluidically connected to the cavity, and wherein the confined space is downstream of the second disc, which is in fluidic communication with the second channel of the sandwich-type holder.

15. The system as claimed in claim 13, wherein the sandwich-type holder comprises a set of O-rings configured on each side of the porous supporting disc within the cavity to restrict leakage of the test gas.

16. The system as claimed in claim 1, wherein at least one of the holders has a disc-shaped profile adapted to accommodate the membrane, wherein the disc-shaped holder is made of a thick transparent acrylic sheet and comprises at least one channel extending between a first end and a second end of the disc, such that the corresponding membrane is longitudinally disposed within the at least one channel, with a cured epoxy layer provided between the surfaces of the membrane and the disc.

17. The system as claimed in claim 1, wherein the test gas is selected from any or a combination of helium, argon, hydrogen, nitrogen, carbon dioxide, methane, ethane, propane, and ethylene.

18. The system as claimed in claim 1, wherein the distinct membranes are selected from Teflon AF®, Silicone Rubber, track-etch hydrophilic polycarbonate, track-etch hydrophobic polycarbonate, track-etch polyimide, nanoporous anodic aluminum oxide, Zeolite ZSM-5, and Zeolite Nay.

19. A method for identification of a test gas, the method comprising the steps of:

allowing a simultaneous parallel flow of the test gas through a plurality of parallelly configured holders, wherein each of the holders comprises a distinct gas permeable membrane disposed of therewithin such that the membranes are configured parallelly and a confined space is created downstream of each of the membranes;

allowing permeation of at least a volume of the supplied test gas through the respective membranes for a predefined time, resulting in accumulation of the permeated test gas in the confined space downstream of the respective membranes; and monitoring, by a pressure sensor configured in the confined spaces downstream of each of the membranes, rate of accumulation of pressurized test gas in the corresponding confined spaces, wherein the monitored rates of test gas pressure accumulation are indicative of permeation rates or a pattern of permeation of the test gas through the corresponding distinct membranes, which facilitates the identification of the test gas based on the simultaneous permeation rates or the pattern of permeation of the pressurized test gas through the distinct and respective gas permeable membranes, comparing the generated first set of signals indicative of the permeation rates or the pattern of permeation of the test gas through the corresponding membranes, to a set of known permeation rates or patterns of permeation of reference gases stored in a reference database, and identifying the test gas based on the permeation rates or the pattern of permeation of the test gas matching the permeation rates or the pattern of permeation of one of the reference gases stored in the reference database.

20. The method as claimed in claim 19, wherein the identifying step further comprises:

receiving, by a computing unit, a first set of data packets corresponding to the rates of permeation or the pattern of permeation of the pressurized test gas in the confined spaces being monitored by the pressure sensors; and performing, by a user or the computing unit, identification of the test gas, based on the first set of data packets by comparison with stored patterns of known reference gases or specific gas mixtures.

* * * * *